US006946259B2

(12) United States Patent
Wahl et al.

(10) Patent No.: US 6,946,259 B2
(45) Date of Patent: Sep. 20, 2005

(54) COMPOSITIONS AND METHODS FOR TREATING CELLS HAVING DOUBLE MINUTE DNA

(75) Inventors: Geoffrey M. Wahl, San Diego, CA (US); Noriaki Shimizu, Hiroshima (JP); Teru Kanda, La Jolla, CA (US); H. Michael Shepard, Rancho Santa Fe, CA (US)

(73) Assignee: The Salk Institute For Biological Studies, La Jolla, CA (US)

( * ) Notice: Subject to any disclaimer, the term of this patent is extended or adjusted under 35 U.S.C. 154(b) by 54 days.

(21) Appl. No.: 09/229,229

(22) Filed: Jan. 12, 1999

(65) Prior Publication Data

US 2005/0123909 A1 Jun. 9, 2005

Related U.S. Application Data

(60) Provisional application No. 60/071,146, filed on Jan. 12, 1998, and provisional application No. 60/077,644, filed on Mar. 11, 1998.

(51) Int. Cl.[7] ........................ G01N 33/52; G01N 33/58; C07K 14/00; C12Q 1/68

(52) U.S. Cl. ................................ 435/7.8; 435/4; 435/6; 435/7.1; 435/40.5; 436/63; 436/64; 530/358

(58) Field of Search .......................... 435/4, 6, 7.1, 7.8, 435/40.5; 436/63, 64; 530/358

(56) References Cited

U.S. PATENT DOCUMENTS 5,229,265 A * 7/1993 Tometsko
5,858,667 A * 1/1999 Dertinger et al.
6,033,849 A * 3/2000 Wahl et al.

OTHER PUBLICATIONS

Hiraoka, Nature (1989) 342: 293–296.*
Abken, Cancer Journal (1995) 8(3): 94–102.*
Robinett, Journal of Cell Biology (1996) 135(6): 1685–1700.*
Karasawa et al., "Detection of c–MYC oncogene amplifications in CML blastic phase patients with double minute chromosomes," *Leukemia Research*, 20(1):85–91, New York, NY (1996).
Ohyashiki et al., "Double–Minute chromosomes appearing in a patient with myelodysplastic syndrome with disease evolution," *Cancer Genetics and Cytogentics*, 79(2):169–172, Elsevier Science Publishing, New York, NY (1995).
Belmont, A.S. et al., "Visualization of Large–Scale Chromatin Structure and Dynamics Using the lac/Operator/lac Repressor Reporter System" *Meth. Cell Biol.* 58:203–222 (1999).
Brison, O., "Gene amplification and tumor progression" *Biochim. Biophys. Acta 1155*:25–41 (1993).

Eckhardt, S.G. et al., "Induction of differentiation in HL60 cells by the reduction of extrachromosmally amplified c–myc" *Proc. Natl. Acad. Sci USA 91*:6674–6678 (Jul. 1994).
Kanda, T. et al., "Histone–GFP fusion protein enables sensitive analysis of chromosome dynamics in living mammalian cells" *Curr. Biol. 8*:377–385 (Mar. 1998).
Livingstone, L.R. et al., "Altered cell cycle arrest and gene amplification potential accompany loss of wild–type p53" *Cell 70*:923–935 (1992).
Shimizu, N. et al., "Selective capture of acentric fragments by micronuclei provides a rapid method for purifying extrachromosomally amplified DNA" *Nature Genet. 12*:65–71 (Jan. 1996).
Von Hoff, D.d. et al., "Hydroxyurea Accelerates Loss of Extrachromosomally Amplified Genes from Tumor Cells" *Cancer Res. 51*:6273–6279 (Dec. 1991).
Yin, Y. et al., "Wild–type p53 restores cell cycle control and inhibits gene amplification in cells with mutant p53 alleles" *Cell 70*:937–948 (1992).
Barker, P.E., "Double minutes in human tumor cells" *Cancer Genet. Cytogenet. 5*:81–94 (1982).
Canute, G.W. et al. "Hydroxyurea accelerates the loss of epidermal growth factor receptor genes amplified as double–minute chromosomes in human glioblastoma multiforme" *Neurosurgery 39*:976–983 (1996).
Carroll, S.M. et al., "Localization of a bidirectional DNA replication origin in the native locus and in episomary amplified murine adenosine deaminase loci" *Mol. Cell. Biol. 13*:2971–2981 (1993).
Cowell, J.K., "Double minutes and homogeneously staining regions: Gene amplification in mammalian cells" *Ann. Rev. Gen. 16*:21–59 (1982).
Cremer, T. et al., "Role of chromosome territories in the functional compartmentalization of the cell nucleus" *Cold Spring Harbor Symp. Quant. Biol. 8*:777–792 (1993).
De Boni, U. and Mintz, A.H., "Curvilinear, three–dimensional motion of chromatin domains and nucleoli in neuronal interphase nuclei" *Science 234*:863–866 (1986).

(Continued)

*Primary Examiner*—Alana M. Harris
*Assistant Examiner*—Anne L. Holleran
(74) *Attorney, Agent, or Firm*—McDermott Will & Emery LLP

(57) ABSTRACT

This invention provides methods by which test substances can be screened for their ability to inhibit, enhance or eliminate double minute (DM) or extrachromosomal DNA by micronucleation in cells. This invention also provides a method for inducing maturation or death of a cell having the capacity to generate micronuclei. It also provides a method of treating a disease in a subject, the cells correlated with the disease having DM and extrachromosomal DNA as well as the capacity to generate micronuclei to capture them. Further provided is a method of detecting chromosomal and extrachromosomal DNA in a cell.

17 Claims, 14 Drawing Sheets

OTHER PUBLICATIONS

Denko, N.C. et al., "The human Ha–ras oncogene induces genomic instability in murine fibroblasts within one cell cycle" *Proc. Natl. Acad. Sci. USA 91*:5124–5128 (1994).

Hamkalo, B.A. et al., "Ultrastructural features of minute chromosomes in a methotrexate–resistant mouse 3T3 cell line" *Proc. Natl. Acad. Sci. USA 82*:1026–1030 (1985).

Heddle, J.A. and Carrano, A.V., "The DNA content of micronuclei induced in mouse bone marrow by γ–irradiation: Evidence that micronuclei arise from acentric chromosomal fragments" *Mutat. Res. 44*:63–69 (1977).

Heddle, J.A. et al., "The induction of micronuclei as a measure of genotoxicity" *Mutat. Res. 123*:61–118 (1983).

Jackson, J.F. and Clement, E.G., "Letter. Nuclear projections and chromosome abnormalities" *Lancet 2*:1270–1271 (1974).

Levan, A. and Levan, G., "Have double minutes functioning centromeres?" *Hereditas 88*:81–92 (1978).

Levan, G. et al., "Double minute chromosomes are not centrometric regions of the host chromosomes" *Hereditas. 83*:83–90 (1976).

Lo Curto, F. and Fraccaro, M., "Letter: Nuclear projections in tumour cells" *Lancet 2*:847 (1974).

Miele, M. et al., "The presence of amplified regions affects the stability of chromosomes in drug–resistant Chinese hamster cells" *Mutat. Res. 219*:171–178 (1989).

Pedeutour, F. et al., "Complex composition and co–amplification of SAS and MDM2 in ring and giant rod marker chromosomes in well–differentiated liposarcoma" *Genes Chromosomes & Cancer 10*:85–94 (1994).

Schubert, I. and Oud, J.L., "There is an upper limit of chromosome size for normal development of an organism" *Cell 88*:515–520 (1997).

Shimizu, N. et al., "Loss of amplified c–myc genes in the spontaneously differentiated HL–60 cells" *Cancer Res. 54*:3561–3567 (1994).

Snapka, R.M., "Gene amplification as a target for cancer chemotherapy" *Oncol. Res. 4*:145–150 (1992).

Snapka, R.M. and Varshavsky, A., "Loss of unstably amplified dihydrofolate reductase genes from mouse cells is greatly accelerated by hydroxyurea" *Proc. Natl. Acad. Sci. USA 80*:7533–7537 (1983).

Toledo, F. et al., "Co–amplified markers alternate in megabase long chromosomal inverted repeats and cluster independently in interphase nuclei at early steps of mammalian gene amplification" *EMBO J. 11*:2665–2673 (1992).

Von Hoff, D.D. et al., "Elimination of extrachromosomally amplified *MYC* genes from human tumor cells reduces their tumorigenicity" *Proc. Natl. Acad. Sci. USA 89*:8165–8169 (1992).

Wahl, G.M. "The importance of circular DNA in mammalian gene amplification" *Cancer Res. 49*:1333–1340 (1989).

Kanda, Teru., "Histone–GFP fusion protein enables sensitive analysis of chromosome dynamics in living mammalian cells", *Current Biology 1998*, (Mar. 10, 1998),pp. 377–385.

* cited by examiner

Figures 1A-1D"
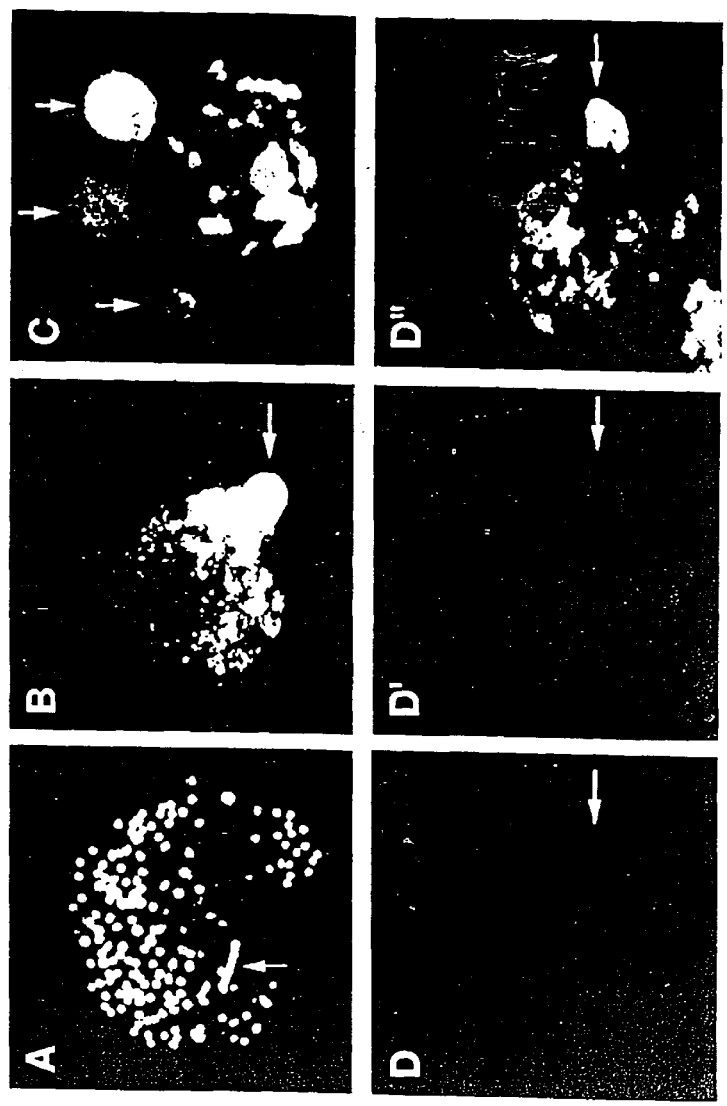

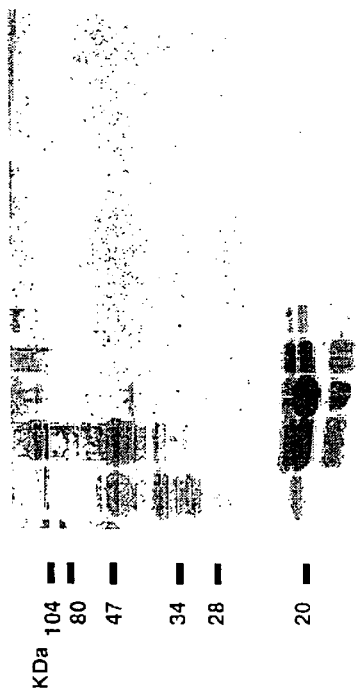
Figures 10B-10D

COMPOSITIONS AND METHODS FOR TREATING CELLS HAVING DOUBLE MINUTE DNA

CROSS-REFERENCE TO RELATED APPLICATIONS

This application claims priority under 35 U.S.C. § 119(e) of U.S. Provisional Application Nos. 60/071,146 and 60/077,644, filed Jan. 12, 1998 and Mar. 11, 1998, respectively.

STATEMENT OF RIGHTS TO INVENTIONS MADE UNDER FEDERALLY SPONSORED RESEARCH

This invention was made with Government support under a grant from the U.S. Department of Army, Grant #DAMD 17-94-J4359. Accordingly, the United States Government has certain rights in this invention.

TECHNICAL FIELD

This invention relates generally to methods for screening for new therapeutic drugs to treat neoplastic conditions such as cancer and the use of the drugs to treat cancer.

BACKGROUND OF THE INVENTION

Throughout and within this application are referenced publications, the full bibliographic citations for which are found within the text of the application or at the end of the specification, immediately preceding the claims. The disclosures of these publications, as well as published patent specifications, books and issued patents are hereby incorporated by reference into the present disclosure to more fully describe the state of the art to which this invention pertains.

It is well known that pharmaceutical research leading to the identification of a new drug generally involves the screening of very large numbers of candidate substances, both before and after, a lead component has been found. This is one factor which makes pharmaceutical research very expensive and time-consuming, so that a method for assisting in the screening process can have considerable commercial importance and utility.

Many pharmaceuticals exert their therapeutic effect by interacting with DNA in the cell. Some pharmaceuticals are targeted to the correction of genetic abnormalities, the accumulation of which leads to a diseased state. For example, mutations in genes commonly occurs during cancer progression and can greatly elevate the frequencies of base alterations or large scale chromosome rearrangements. For example, defects in cell cycle control pathways involving the p53 tumor suppressor gene create a permissive environment in which cells with aneuploidy, chromosome translocations and gene amplification arise at high frequency in response to stresses created by antimetabolites or oncogene overexpression (Livingstone, et al. (1992); Yin, et al. (1992) and Denko, et al. (1994)).

The types of aberrant chromosomal structures generated in cells with defective repair and cell cycle control functions are likely to be constrained by nuclear structure. For example, chromosomes with very long arms tend to generate nuclear projections variously referred to as "blebs" or "buds" occur (Ruddle (1962); Lo and Fraccaro (1974); Toledo, et al. (1992) and Pedeutour, et al. (1994)). A recent study in peas demonstrated that excessive DNA within a single chromosome arm generated a nuclear projection which was cut when the cell division plate formed after telophase (Schubert and Oud (1997)). Sequences enclosed in such projections are often detected in micronuclei, suggesting that projections can be precursors of micronuclei (Toledo, et al. (1992) and Pedeutour, et al. (1994)), and that the chromosomal sequences they contain can be lost from the nucleus. These data indicate that a maximum allowable size exists for each chromosome arm within the nuclei of specific cell types.

Circular, autonomously replicating DNA fragments such as double minute chromosomes (DMs) also frequently generated in cancer cells (Barker (1982); Cowell (1982) and Benner, et al. (1991)). These structures encode proteins that provide survival advantages in vivo, or resistance to a variety of chemotherapeutic agents in vitro (see Wahl (1989); Brison (1993); Von Hoff, et al. (1992); Shimizu, et al. (1994) and Eckhardt, et al. (1994)). DMs replicate using cellular replication origins (Carroll, et al. (1993)), but lacking centromeres, they do not segregate by the same mechanism employed by chromosomes. Consequently, DMs are lost spontaneously in the absence of selection. Drugs such as hydroxyurea significantly increase the loss rate of DMs in human and rodent cell lines (Snapka and Varshavsky (1983); Von Hoff, et al. (1991); Von Hoff, et al. (1992); Eckhardt, et al. (1994) and Canute, et al. (1996)). DM elimination results in increased drug sensitivity, reduced tumorigenicity, or differentiation, depending on the proteins expressed by DM-encoded genes (Snapka and Varshavsky (1983); Snapka (1992); Von Hoff, et al. (1992); Eckhardt, et al. (1994) and Shimizu, et al. (1994)). For this reason, identifying the mechanisms by which DMs are eliminated could enable the development of new or more selective chemotherapeutic strategies since DMs are uniquely found in cancer cells, and chromosome loss should not be induced by such treatments.

Like abnormally long chromosome arms, DMs have also been reported to be preferentially incorporated within micronuclei that are removed from the cell (Von Hoff, et al. (1992) and Shimizu, et al. (1996)). It is clear that small size alone does not guarantee selective enclosure of DNA fragments within micronuclei since a centric minichromosome the size of a typical DM is effectively excluded from micronuclei (Shimizu, et al. (1996)). This observation is consistent with the classical mechanism of micronucleus formation which involves the enclosure of lagging acentric chromosome fragments as nuclear membranes reform at the end of mitosis (Heddle and Carrano (1977) and Heddle, et al. (1983)). Thus, one would expect post-mitotic enclosure of DMs within micronuclei since they typically lack functional centromeres (Levan, et al. (1976)). However, DMs appear to associate with chromosomes or nucleoli, which may enable most of them to evade such a post-mitotic mechanism. The ability of DMs to "hitch-hike" by association with mitotic chromosomes or nucleoli provides one explanation why few micronuclei were detected at the midbody in a cell line containing numerous DMs (Levan and Levan (1978)), and their surprisingly efficient partitioning to daughter cells in some cell lines (Levan and Levan (1978) and Hamkalo, et al. (1985)). However, the interphase behavior of normal chromosomes and DMs may differ because DMs lack the centromeres and/or telomeres which position chromosomes in restricted territories and produce a choreographed set of chromosome movements during S-phase (De and Mintz (1986) and Cremer et al. (1993)). It has not been determined whether acentric DM DNA occupies positions different from chromosomes in interphase, and whether this could enable their removal from the nucleus by a budding process like that observed for abnormally long chromosomes (Ruddle (1962); Jackson and Clement (1974); Lo and Fraccaro (1974); Miele, et al. (1989) and Toledo, et al. (1992)).

DISCLOSURE OF THE INVENTION

This invention relates to screening of candidate substances for potential as pharmaceutical agents. More particularly, it provides a method by which test substances can be screened for their ability to inhibit, enhance or eliminate double minute DM or extrachromosomal DNA from cells by micronucleation.

This invention also provides a method for inducing maturation or death of a cell having DM or extrachromosomal DNA. A suitable cell is contacted with an agent as defined herein so that DM or extrachromosomal DNA is eliminated from the cell by the process of micronucleation.

This invention further provides a method of treating a disease in a subject by administering to the subject an effective amount of an agent as defined herein.

Further provided by this invention is a method of detecting chromosomal and extrachromosomal DNA in a cell. The method requires inserting into the cell a detectably labeled protein, wherein the protein specifically associates with the chromosomal DNA in the cell then detecting the label, thereby detecting chromosomal and extrachromosomal DNA in the cell.

BRIEF DESCRIPTION OF THE DRAWINGS

FIGS. 1A through D" show nuclear budding selectively entrapping DMs. COLO 320DM cells fixed with methanol/acetic acid were treated with RNAse, hybridized with biotinylated DNA from purified micronuclei, and the hybridized probe was detected by FITC conjugated streptavidin. The nuclei were counterstained with propidium iodide (PI). FIG. 1A is a prometaphase figure which shows both the specificity of the probe for DM-painting and documents the peripheral location of DMs around the prometaphase chromosomes. One chromosomally integrated HSR region is indicated by an arrow. These DMs are selectively incorporated into the nuclear buds formed in the interphase nuclei (FIGS. 1B to 1D, arrowed). DM capture by buds appears to be very selective because the three dense PI positive signals obvious in the nuclear bud (FIG. 1D) label intensely with the FITC FISH probe (FIG. 1D'), and the merged image (FIG. 1D").

In FIG. 3A, the treated cells were fixed with methanol/acetic acid and hybridized with c-myc cosmid probe. The numbers of micronuclei that were stained brightly with c-myc probe were scored and expressed as "frequency of c-myc$^+$ micronuclei (%)" relative to the number of interphase nuclei scored (more than 1000 for each point). In FIG. 3B, the cells were pulse-labeled with BrdU (for 30 min) at the end of the drug treatment, and analyzed by flow cytometry as described below to determine the fraction of cells in G1, S, and G2/M.

In FIGS. 6A and 6B a culture of rapidly growing COLO-320DM cells was pulse labeled with 10 μM BrdU for 1 hr. The nuclei were isolated, fixed with PFA, hybridized with the biotinylated DM-painting probe, and detected using FITC-conjugated streptavidin, as in FIG. 4. Sites at which BrdU was incorporated were detected with an anti-BrdU mouse monoclonal antibody followed by rhodamine conjugated anti-mouse immunoglobulin. The double labeled nuclei were examined using a confocal laser scanning microscope. The images of BrdU, FISH, and the merged images (the red pseudocolor for BrdU and the green pseudocolor for FISH) are shown for two representative fields. Nuclear buds that selectively entrap DMs are indicated by arrows, and the cells that were not in S-phase during the pulse label (BrdU-) are indicated by arrowheads. FIG. 6C summarizes the analysis of apoptosis in COLO 320DM cells was done using the TUNEL method as described below. This representative photograph is from one experiment in which COLO 320DM cells were treated with 100 μM HU for 3 days. The arrow points to a bud in a cell that is not undergoing apoptosis, while the arrowhead points to an apoptotic cell in the same field.

FIG. 7A shows cells grown on cover slips and as treated above, were fixed, and stained by DAPI. The number of micronuclei were scored and expressed as the frequency of micronuclei (%) relative to the number of interphase nuclei scored (more than 1000 for each point). In FIG. 7B, cell cycle effects of these drugs were examined as in FIG. 2B. In FIGS. 7C and 7D, the culture of WS1 neo (triangles) or WS1 E6 (circles) were synchronized at G1V/S-boundary by the procedure described below, and were released into growth medium. In FIG. 7C, progression through S-phase or M-phase was monitored by the incorporation of [$^3$H] thymidine (closed symbols) or the fraction of mitotic cells determined by microscopic detection of metaphase figures (open symbols). In FIG. 7D, the cells on the cover slips were fixed, stained with DAPI, and the frequencies of micronuclei relative to the number of interphase nuclei were scored. More than 500 nuclei were counted for each point and the results are expressed as mean±S.D for WS1 neo and WS1-E6 cells (3 independent determinations for each strain; the error bars for WS1 neo data points were smaller than the sizes of the symbols). Nuclear budding frequencies were determined on the same slides as used to determine micronucleation index (more than 1000 nuclei for each point).

FIGS. 10A through 10D show H2B-GFP is incorporated into mononucleosomes. FIG. 10A shows micrococcal nuclease digestion of nuclei of HeLa cells and HeLa cells with H2B-GFP expression. Isolated nuclei were digested for 0, 1, 5, 10, 15, 30, and 60 min. The DNA protected from digestion by the binding of nucleosomal core proteins was purified and analyzed as detailed in materials and methods. FIG. 10B shows a sucrose gradient analysis of mononucleosome populations. The mononucleosome protein-DNA complexes, prepared by micrococcal nuclease digestion, were purified through parallel 5–30% sucrose gradients. Proteins from each fraction were extracted and analyzed by 15% SDS-PAGE and Coomassie staining. H2B-GFP protein (approx. 45 kDa) and native core histone proteins are indicated. In FIG. 10C, the same aliquots of the protein samples were electrophoresed and analyzed by Western blotting using anti-human H2B antibody. H2B-GFP protein and native H2B protein are indicated. In FIG. 10D, DNA was extracted from each fraction and analyzed by 1.5% agarose gel.

FIG. 11A is a GFP histogram of HeLa cells and H2B-GFP expressing cells. FIG. 11B is a DNA histogram of the same cells as shown in FIG. 11A determined by PI staining.

FIG. 12E shows fixed chromosome spreads of HeLa cells expressing H2B-GFP. GFP localization (left) and DAPI staining (right) are shown.

MODES FOR CARRYING OUT THE INVENTION

Figures 2A, 2B, 2C, 2D, 2E, 2F:
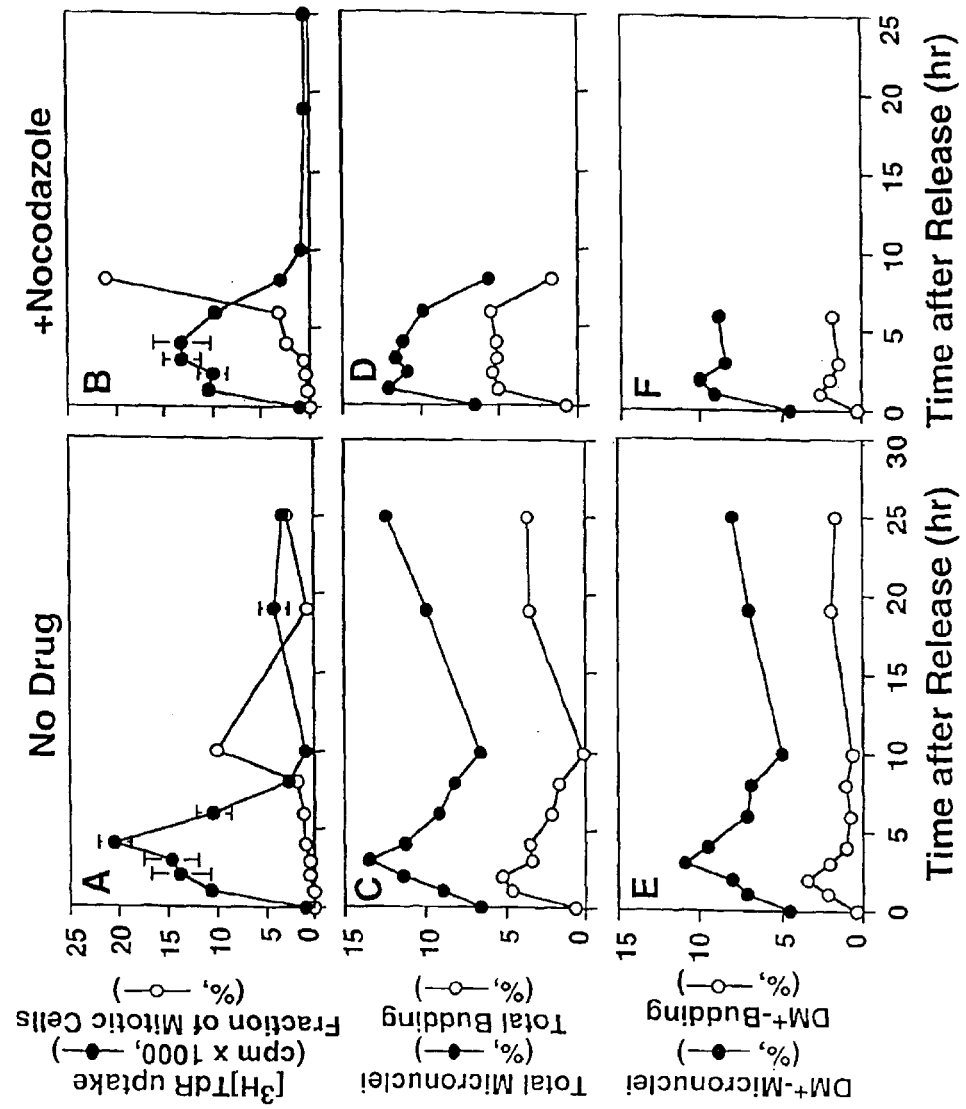
FIGS. 2A through 2F show formation of micronuclei and nuclear buds in a synchronized culture of COLO 320DM cells. COLO 320DM cells were synchronized at the G1/S boundary using a two step procedure as described below. The culture was divided into two portions, and released in the absence of any drug (FIGS. 2A, 2C and 2E), or the presence of 0.4 mg/ml of nocodazole (FIGS. 2B, 2D and 2F). [$^3$H]thymidine incorporation (closed circles), and the fraction of mitotic cells (open circles) were determined to monitor the synchronous progression through S- and M-phases, respectively (FIGS. 2A and 2B). The numbers of total micronuclei (closed circles) and total nuclear buds (open circles) were determined in slides stained with DAPI (FIGS. 2C and 2D). The numbers of DM+micronuclei (closed circles) or DM+nuclear buds (open circles) were determined in the slides hybridized with the purified micronuclei probe (FIGS. 2E and 2F). These values are expressed as the frequency relative to the number of interphase nuclei scored (more than 1000 for each point).

This invention exploits the discovery that acentric, autonomously replicating extrachromosomal structures called double minute chromosomes (DMs) frequently mediate oncogene amplification in human tumors. Removal of DMs from the nucleus by micronucleation that is initiated by budding of the nuclear membrane during S-phase are shown by the inventors to induce cell maturation, differentiation and death.

Thus, this invention provides a screen for identifying a potential therapeutic agent and for a method for inducing maturation or death of a suitable cell. Suitable test cells or suitable cells for the practice of this invention include those having DM or extrachromosomal DNA and the capacity to eliminate this DNA by the process of micronucleation. These cells include, but are not to be limited to, a procaryotic cell such as a bacterial cell or a yeast cell. Also included is a eucaryotic cell, such as a rat, avian, murine, simian, mammalian, including pets and livestock, or a human cell.

For the purposes of this invention, an "agent" is intended to include, but not be limited to, a small organic molecule, a compound, a composition, a DNA molecule, an RNA molecule, a protein, a polypeptide, or a fusion protein. It should be understood, although not always explicitly stated that the agent is used alone or in combination with another agent, having the same or different biological activity as the agents identified by the inventive screen. The agents and methods are also intended to be combined with other therapies.

As used herein, the term "inducing maturation or death of a cell" is intended to include apoptosis, necrosis or any other means of preventing cell division, reduced tumorigenicity, loss of pharmaceutical resistance, maturation, differentiation or reversion of the neoplastic phenotype of the cells. As noted above, cells having DM or extrachromosomal DNA are suitably treated by this method. These cells can be identified by any method known in the art that allows for the identification of amplified chromosomal or extra chromosomal DNA. Such methods include, but are not limited to Southern hybridization (see Example II D, below and Sambrook et al. (1988)), FISH (see Example II B, below, U.S. Pat. Nos. 5,665,549; 5,633,365; and 5,545,524), fluorescent activated cell sorting (FACS) (see Example II C, below) centrifugal fractionization and histone-GFP labeling (see Example I, below). Some cell types are known to contain micronuclei, e.g., cells containing an absent or a defective tumor suppressor protein and neoplastic or tumor cells. The absence or presence of a defective tumor suppressor protein can be the result of defective tumor suppressor gene. Tumor suppressor genes are termed "recessive" because mutation in these genes causes loss of function. Loss or inactivation of both alleles is required before tumors are formed but mutation in one allele is responsible for the inherited predisposition to cancer in human populations.

The method can be practiced in vitro, ex vivo or in vivo. When practiced in vitro, the method provides a powerful assay and screen to determine whether and how an agent or combination of agents modulates the reduction or elimination of DM or extrachromosomal DNA from a cell. In some instances, it may be desirable to enhance elimination, while in other instances, it may be desirable to reduce or inhibit the elimination of DM or extrachromosomal DNA by the process of micronucleation, as when one wishes to inhibit apoptosis. Accordingly, this invention also provides a method of screening for a potential therapeutic agent by first providing a sample of suitable cells. The cells are contacted with the potential therapeutic agent under suitable conditions that favor insertion of the agent into the cells. After an appropriate period, the cells are then assayed for the presence of DM and/or extrachromosomal DNA in the cell or in the cell culture or supernatant. In one embodiment, the reduction or elimination of DM or extrachromosomal DNA is a positive indication that the agent is a potential therapy. In an alternative embodiment, to reduce or inhibit the elimination of micronuclei may be desired.

Thus, to practice the method in vitro, suitable cell cultures or tissue cultures are first provided. The cell is a cultured cell or a genetically modified cell. Alternatively, the cells can be from a tissue biopsy. The cells are cultured under conditions (temperature, growth or culture medium and gas ($CO_2$)) and for an appropriate amount of time to attain exponential proliferation without density dependent constraints. It also is desirable to maintain an additional separate cell culture; one which does not receive the agent being tested as a control.

As is apparent to one of skill in the art, suitable cells may be cultured in microtiter plates and several agents may be assayed at the same time by noting phenotypic changes or cell death.

When a potential agent is determined to have the required biological activity, the agent may be added to cells to induce maturation or death of the cells. Accordingly, this invention also provides a method for inducing maturation or death of a cell, wherein the cell contains DM or extrachromosomal DNA and has the capacity to undergo micronucleation. The method includes contacting the cell with an agent that induces or enhances elimination DM or extrachromosomal DNA from the cell by micronucleation. The agent is contacted with the cells under conditions which favor maturation or death of the cells. When the agent is a composition other than a DNA or RNA nucleic acid molecule, the suitable conditions may be directly added to the cell culture or added to culture medium. As is apparent to those skilled in the art, an "effective" amount must be added which can be empirically determined.

When the agent is a nucleic acid, it can be added to the cell cultures by methods well known in the art, which includes, but is not limited to, calcium phosphate precipitation, microinjection or electroporation. Alternatively or additionally, the nucleic acid can be incorporated into an expression or insertion vector for incorporation into the cells. Vectors that contain both a promoter and a cloning site into which a polynucleotide can be operatively linked are well known in the art. Such vectors are capable of transcribing RNA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as baculovirus and retrovirus, bacteriophage, cosmid, plasmid, fungal vectors and other recombination vehicles typically used in the art which have been described for expression in a variety of eukaryotic and prokaryotic hosts, and may be used for gene therapy as well as for simple protein expression.

Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens, e.g., TCR, CD3 or CD4. Liposomes that also comprise a targeting antibody or fragment thereof can be used in the methods of this invention. This invention also provides the targeting complexes for use in the methods disclosed herein.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV40 for mRNA stability; SV40 polyoma origins of replication and ColE1 for proper episomal replication; versatile multiple cloning sites; and T7 and SP6 RNA promoters for in vitro transcription of sense and antisense RNA. Other means are well known and available in the art.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eukaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG (Sambrook et al., supra.). Similarly, an eukaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general. Expression vectors are useful to produce cells that express the invention receptor.

One can determine if the object of the method, i.e., reduction or elimination of DM or extrachromosomal DNA by micronucleation from the cell has been achieved by a reduction of life of the cell, differentiation of the cell or assaying for apoptosis. Cellular differentiation can be monitored by histological methods or by monitoring for the presence or loss of certain cell surface markers, which may be associated with an undifferentiated phenotype, e.g. CD34 on primative hematopoietic stem cells.

To monitor apoptosis, cells are plated at a concentration of 2.5×10⁵ cells/well onto glass coverslips. Approximately two days later, after the cells had adhered and spread, cells are fixed, stained with propidium iodide and mounted. Apoptotic and non-apoptotic cells are quantitated based on nuclear morphology using fluorescence microscopy and the percentage of non-apoptotic cells loss calculated. A minimum of 100 cells is counted for each sample, and each experiment should be done at least in duplicate. Since a small fraction of cells in any normally growing cell culture is undergoing apoptosis, spontaneous apoptosis in untreated or treated samples also is quantitated. The percentage of non-apoptotic cells are then normalized by correcting for the frequency of spontaneous apoptosis in the untreated samples. For electron microscopy, cells were fixed and processed as per standard electron microscopy procedures. Secondary assays of cell death may be uses, for example, MTT conversion assay and crystal violet staining, as known in the art.

The methods of this invention also can be practiced ex vivo using a modification of the method described in U.S. Pat. No. 5,399,346.

Kits containing the agents and instructions necessary to perform the screen and in vitro method as described herein also are claimed.

This invention also provides a method of treating a disease wherein the disease is characterized by the presence of cells in the subject containing DM or extrachromosomal DNA and the capacity to eliminate the DNA by micronucleation. The method is administering to the subject an effective amount of an agent that induces or enhances elimination of the DNA by micronucleation.

When the subject is an animal such as a rat or mouse, the method provides a convenient animal model system which can be used prior to clinical testing of the therapeutic agent. In this system, a candidate agent is a potential drug if DM or extrachrosomal DNA are reduced or eliminated as determined by a cellular assay or if symptoms associated or correlated to the presence of cells containing DM or extrachromosomal DNA are ameliorated, each as compared to an untreated animal having the pathological cells. It also can be useful to have a separate negative control group of cells or animals which are healthy and not treated, which provides a basis for comparison. Administration of an agent selected from the group consisting of hydroxyurea or guanazole is useful as a positive control, in vivo and in vitro.

In one embodiment, the agent used in the methods as described herein are selected from the group consisting of hydroxyurea, guanozole, or derivatives thereof. For example, the agent has the structure:

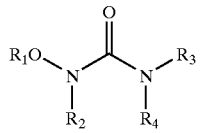

wherein $R_1$ is H, alkyl, aryl, substituted aryl, heteroaryl, substituted heteroaryl, acyl or —(CH$_2$)$_n$—X, wherein n is an integer from 1 to 4, X is substituted alkyl, alkenyl or alkynyl, and substituents are selected from the group consisting of halo, —OH, —NR$_2$, —OR, —C(O)OR, —OC(O)R, amide and acyl wherein R is H, alkyl or aryl;

$R_2$ is H, alkyl, aryl, substituted aryl, heteroaryl, substituted heteroaryl, —C(O)R' or —(CH$_2$)$_n$—X, wherein n is an integer from 1 to 4, X is substituted alkyl, alkenyl or alkynyl, and wherein R' is alkyl or aryl and substituents are as defined above;

$R_3$ is H, alkyl, aryl, substituted aryl, heteroaryl, substituted heteroaryl, OR", NR"$_2$ or —(CH$_2$)$_n$—X, wherein n is an integer from 1 to 4, X is substituted alkyl, alkenyl or alkynyl, and substituents are selected from the group consisting of —OH, —NR"$_2$, —OR", —C(O)OR", —OC(O)R", amide and acyl wherein R" is H, alkyl or aryl; and $R_4$ is H, alkyl, aryl, substituted aryl, heteroaryl, substituted heteroaryl, or —(CH$_2$)$_n$—X, wherein n is an integer from 1 to 4, X is substituted alkyl, alkenyl or alkynyl, and substituents are selected from the group consisting of —OH, —NR'''$_2$, —OR''', —C(O)OR''', —OC(O)R''', amide and acyl wherein R''' is H, alkyl or aryl.

In an alternative method, the agent has the structure:

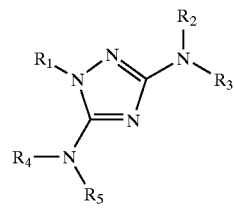

wherein $R_1$ is H, alkyl, aryl, substituted aryl, heteroaryl, substituted heteroaryl, acyl or —(CH$_2$)$_n$—X, wherein n is an integer from 1 to 4, X is substituted alkyl, alkenyl or alkynyl, and substituents are selected from the group consisting of halo, —OH, —NR$_2$, —OR, —C(O)OR, —OC(O)R, amide and acyl wherein R is H, alkyl or aryl;

$R_2$ and $R_4$ are independently H, alkyl, aryl, substituted aryl, heteroaryl, substituted heteroaryl, OR', NR'$_2$ or —(CH$_2$)$_n$—X, wherein n is an integer from 1 to 4, X is substituted alkyl, alkenyl or alkynyl, and substituents are selected from the group consisting of —OH, —NR'$_2$, —OR', —C(O)OR', —OC(O)R', amide and acyl wherein R' is H, alkyl or aryl; and $R_3$ and $R_5$ are independently H, alkyl, aryl, substituted aryl, heteroaryl, substituted heteroaryl or —(CH$_2$)$_n$—X, wherein n is an integer from 1 to 4, X is substituted alkyl, alkenyl or alkynyl, and substituents are selected from the group consisting of —OH, —NR"$_2$, —OR", —C(O)OR", —OC(O)R", amide and acyl wherein R" is H, alkyl or aryl.

Hydroxyurea and guanazole are commercially available and serve as starting material for the derivatives. Using a modification of the teachings of U.S. Pat. Nos. 5,549,974; 5,639,603 and 5,679,773, derivatives of these small organic compounds are synthesized and assayed for biological activity using the methods of this invention.

These agents of this invention and the above noted compounds and their derivatives may be used for the preparation of medicaments for use in the methods described herein.

The agents identified herein as effective for their intended purpose can be administered to subjects or individuals susceptible to or at risk of developing a disease correlated to the presence of DM and/or extrachromosomal DNA in cells, such as cancer. When the agent is administered to a subject such as a mouse, a rat or a human patient, the agent can be added to a pharmaceutically acceptable carrier and systemically or topically administered to the subject. To determine patients that can be beneficially treated, a tumor sample is removed from the patient and the cells are assayed for the presence of DM, extrachromosomal DNA or micronuclei. Therapeutic amounts can be empirically determined and will vary with the pathology being treated, the subject being treated and the efficacy and toxicity of the agent. When delivered to an animal, the method is useful to further confirm efficacy of the agent. As an example of an animal model, groups of nude mice (Balb/c NCR nu/nu female, Simonsen, Gilroy, Calif.) are each subcutaneously inoculated with about $10^5$ to about $10^9$ hyperproliferative, cancer or target cells as defined herein. When the tumor is established, the agent is administered, for example, by subcutaneous injection around the tumor. Tumor measurements to determine reduction of tumor size are made in two dimensions using venier calipers twice a week. Other animal models may also be employed as appropriate.

Administration in vivo can be effected in one dose, continuously or intermittently throughout the course of treatment. Methods of determining the most effective means and dosage of administration are well known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents can be found below.

The agents and compositions of the present invention can be used in the manufacture of medicaments and for the treatment of humans and other animals by administration in accordance with conventional procedures, such as an active ingredient in pharmaceutical compositions.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including oral, rectal, nasal, topical (including transdermal, aerosol, buccal and sublingual), vaginal, parental (including subcutaneous, intramuscular, intravenous and intradermal) and pulmonary. It will also be appreciated that the preferred route will vary with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient. Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

While it is possible for the agent to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with the other ingredients of the formulation and not injurious to the patient.

Formulations include those suitable for oral, rectal, nasal, topical (including transdermal, buccal and sublingual), vaginal, parenteral (including subcutaneous, intramuscular, intravenous and intradermal) and pulmonary administration. The formulations may conveniently be presented in unit dosage form and may be prepared by any method well known in the art of pharmacy. Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets, each containing a predetermined amount of the active ingredient; as a powder or granules; as a solution or suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention may be formulated as an ointment, cream, suspension, lotion, powder, solution, paste, gel, spray, aerosol or oil. Alternatively, a formulation may comprise a patch or a dressing such as a bandage or adhesive plaster impregnated with active ingredients and optionally one or more excipients or diluents.

If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the agent through the skin or other affected areas. Examples of such dermal penetration enhancers include dimethylsulfoxide and related analogues.

The oily phase of the emulsions of this invention may be constituted from known ingredients in an known manner.

While this phase may comprise merely an emulsifier (otherwise known as an emulgent), it desirably comprises a mixture of at lease one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulphate.

The choice of suitable oils or fats for the formulation is based on achieving the desired cosmetic properties, since the solubility of the active compound in most oils likely to be used in pharmaceutical emulsion formulations is very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with a suitable base comprising, for example, cocoa butter or a salicylate.

Formulations suitable for vaginal administration may be presented as pessaries, tampons, creams, gels, pastes, foams or spray formulations containing in addition to the agent, such carriers as are known in the art to be appropriate.

Formulations suitable for nasal administration, wherein the carrier is a solid, include a coarse powder having a particle size, for example, in the range of about 20 to about 500 microns which is administered in the manner in which snuff is taken, i.e., by rapid inhalation through the nasal passage from a container of the powder held close up to the nose. Suitable formulations wherein the carrier is a liquid for administration as, for example, nasal spray, nasal drops, or by aerosol administration by nebulizer, include aqueous or oily solutions of the agent.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of a agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies.

Further provided by this invention is a method of detecting chromosomal and extrachromosomal DNA in a cell. The method comprising the steps of first inserting into the cell a detectably labeled protein, wherein the protein specifically associates with the chromosomal and extrachromosomal DNA in the cell then detecting the label, thereby detecting chromosomal and extrachromosomal DNA in the cell. In one embodiment, the protein is histone or an analog thereof having conservative amino acid substitutions, as well as fusion proteins. In one embodiment, the detectable label is a fluorescent label, e.g., *Aequorea victoria* green fluorescent protein, which may be modified to have a cayenne or yellow fluorescence. Alternatively, avidin, strepavidin or biotin may be used. In an alternative embodiment, the insertion step comprises contacting the cell with a vector comprising a DNA encoding detectably labeled histone fusion protein.

The above method also provides methods for analyzing chromosomal behavior in vivo, monitoring chromosomal movement, i.e., loss or translocation of chromosomal fragments in cells, detecting a pathological cell characterized by the presence of DM or extrachromosomal DNA in the cell, and methods of monitoring the progression of such as pathology in a patient. Each of these methods include inserting into the cell a detectably labeled protein, wherein the protein specifically associates with the chromosomal and extrachromosomal DNA in the cell then detecting the label, thereby detecting chromosomal and extrachromosomal DNA in the cell. The presence, absence or location of the chromosomal region of interest can then be correlated with previous sample analysis or normal cells to complete the analysis and monitor chromosomal aberrations and/or changes. A pathological cell also can be detected by this method, wherein the pathological cell has amplified or extrachromosomal DNA. Cells such as cancer, e.g., prostate cancer, and/or neoplastic cells can be detected.

The following examples are provided to illustrate, but not limit, the invention.

EXPERIMENTAL EXAMPLES

I. Correlation of DM and Extrachromosomal DNA with Loss of Phenotype

A. Cell Culture

Human COLO 320DM (ATCC Accension No. CCL 220) and COLO 320HSR (ATTC Accension No. CCL 220, 1) neurodendocrine tumor cells were obtained from American Type Culture Collection, 12301 Parklawn Drive, Rockville Md., 20853, U.S.A. and single cell subclones were obtained by limiting dilution (Von Hoff, et al. (1988)). The locations of amplified c-myc genes to DMs or HSRs were confirmed by FISH using c-myc cosmid DNA. The cells were grown in RPMI1640 medium supplemented with 10% fetal bovine serum (FBS). The WS1 human embryonic skin fibroblast, obtained from American Type Culture Collection (CRL 1502), was cultured in Dulbecco's modified Eagle's medium (DMEM) supplemented with 10% heat-inactivated, dialyzed FBS, and 1×MEM nonessential amino acids. WS1 neo and WS1 E6 were kind gifts of Dr. S. Linke, and were generated by infecting WS1 with retroviral vectors expressing genes encoding either neomycin resistance or both neomycin resistance and the E6 protein from human papilloma virus 16, respectively (Linke, et al. (1996)). RPE-h (normal human retinal pigmented epithelial cells) and its neo and E6 derivatives were also kindly provided by Dr. S. Linke and the parental cells were obtained from Cell Genesys, Inc. (Foster City, Calif.). Epithelial cells were cultured in the same way as WS1.

B. Chemicals

Aphidicolin, 5-bromo-2'-deoxyuridine (BrdU), coumarin (1,2-benzopyrone), deferoxamine mesylate (desfemoxamine mesylate), DMSO, hydroxyarea (HU), nicotinamide, thymidine and nocodazole (Methyl-(5-(2-thienylcarbonyl)-1H-benzimidazol-2-YL)carbamate) were obtained from Sigma (St. Louis, Mo.). Guanazole (3,5-diamino-1,2,4-triazole) was from Aldrich (Milwaukee, Wis.), PALA (N-phosphonacetyl-L-aspartate) was provided by the Drug Biosynthesis & Chemistry Branch, Developmental Therapeutics Program, Division of Cancer Treatment, National Cancer Institute (Bethesda, Md.).

C. Cell Cycle Analysis

Cell cycle distribution was analyzed using flow cytometry as described previously (Yin, et al. (1992) and Di Leonardo, et al. (1994)). Cells treated with the indicated concentrations of drugs for the indicated times were labeled with 10 $\mu$M BrdU for 30 min. The cells were collected, fixed with 70% ethanol, with 0.1N HCl containing 0.5% Triton X-100, followed by boiling for 10 min and rapid cooling to denature the DNA. The nuclei were then incubated with FITC-conjugated anti-BrdU antibodies (Boehringer Mannheim) and counterstained with 2 $\mu$g/ml of propidium iodide (PI) containing RNAse (200 $\mu$g/ml). Samples were analyzed using a Becton Dickinson FACScan. Ten thousand events were collected for each sample. Data was analyzed using Sun Display as described previously (Yin, et al. (1992) and Di Leonardo, et al. (1994)).

D. Quantification of Micronuclei

Micronuclei containing DM sequences in COLO 320DM cells (FIGS. 2 and 3) were detected by preparing chromosome spreads using standard hypotonic swelling conditions (Lawce and Brown (1991)), followed by hybridization with a biotinylated c-myc cosmid probe as described previously (Shimizu, et al. (1996)). Total micronuclei (FIG. 3) were determined by staining chromosome spreads with DAPI (Sigma; 1 $\mu$g/ml in VectaShield, Vector Inc.). The adherent cells (WS1, RPE-h and their derivatives) were grown on cover slips, fixed with cold acetone (−20° C. for 5 min) followed by cold methanol (−20° C. for 5 min), re-hydrated with PBS and stained with DAPI (1 $\mu$g/ml in VectaShield). The numbers of total or DM-enriched micronuclei were scored using 60× or 100× objectives and Zeiss fluorescence microscope equipped with appropriate epifluorescence filters. The results are expressed as "Frequency of micronuclei (%)" relative to the number of interphase nuclei scored (at least 1000 for each point).

E. Cell Synchronization

Synchronization was performed as described previously (Stein, et al. (1994)). Rapidly growing COLO 320DM cells were first arrested in early S-phase using excess thymidine (2 mM) for 17 hours. The cells were then washed with growth medium, released into growth medium containing 25 $\mu$M 2'-deoxycytidine for 12 hours (to reverse thymidine toxicity) and then incubated in 2.5 $\mu$g/ml aphidicolin for 17 hours to arrest cells as they enter S-phase. The arrested cells were washed with growth medium, and then either released into medium lacking drug or into medium containing nocodazole (0.4 $\mu$g/ml). Cell cycle progression was monitored using incorporation of [$^3$H]thymidine (Stein, et al. (1994)). To monitor the progression through mitosis, a portion (1 ml) of culture was fixed by paraformaldehyde (PFA; 2%) and stained with DAPI. The frequency of cells in mitosis was scored using fluorescence microscopy. WS1 E6 cells were synchronized by seeding them at low density in 15 cm dishes with or without cover slips (18×18 mm). The day after subculture, the medium was removed and replaced with a medium containing 0.1% FCS, followed by the culture for an additional 48 hours. Cells arrested at G0 by serum deprivation were released into growth medium containing 5 $\mu$g/ml aphidicolin for 15 hours to arrest them at the beginning of S-phase. Cells were released into S-phase by replacing the medium with fresh growth medium lacking drug. Progression into S-phase was monitored by the incorporation of [$^3$H]thymidine (Stein, et al. (1994)). Concurrently, cover slips were removed, fixed with acetone and methanol, stained by DAPI, and the frequency of micronuclei, nuclear budding and mitotic cells were scored as described above.

F. TUNEL Assay

TUNEL assay was done according to a previously published procedure (Gavrieli, et al. (1992)) and modified as described below. In brief, COLO 320DM cells were fixed in 2% PFA (10 min at room temperature), and centrifuged onto a glass slide using a cytospin apparatus. The cells were further fixed in cold methanol (−20° C., 5 min) followed by cold acetone (−20° C., 5 min). The slides were rehydrated in PBS, then equilibrated in reaction buffer (200 mM sodium cacodylate, 1 mM $MgCl_2$, 1 mM $\beta$-mercaptoethanol, pH 7.2) for 15 min at room temperature. The end-labeling reaction was done by incubating the slides with the reaction buffer containing 10 $\mu$M biotin-dUTP (Boehringer Mannheim GmbH, Germany), and 0.3 units/$\mu$l of terminal deoxynucleotidyl transferase (Toyobo Co., Osaka, Japan), for 60 min at 37° C. The slides were washed extensively, blocked with 20% FCS, and the incorporated biotin was detected using FITC conjugated streptavidin as in the protocol for FISH (see below). The slides were treated with RNAse A (100 $\mu$g/ml 37° C., for 20 min), counterstained with PI, and observed under the conditions used for FISH.

G. Probe Preparation and FISH

Preparation of probe from purified micronuclei was as described (Shimizu, et al. (1996)), except that DNA in the purified micronuclei was directly used for biotin-labeling by using BioPrime DNA Labeling System (Life Technologies Inc. Gaithersburg, Md.). FISH using standard methanol/acetic acid-fixed nuclei was performed as described previously (Shimizu, et al. (1996)). Assessments of DM localization by confocal microscopy required the following procedure to preserve the spherical shape of the nuclei. This protocol, based on that developed for human lymphocytes (Ferguson and Ward (1992) and Vourc'h, et al. (1993)), could not be applied directly to COLO 320DM due to severe nuclear aggregation. The modified procedure involves pelleting 10 ml of COLO 320DM cells by centrifugation at 260×g for 5 min, followed by complete removal of the supernatant. The cells were gently suspended in 50 $\mu$l of growth medium, and 10 ml of prewarmed (37° C.) 75 mM KCl, 2 mM $CaCl_2$ was added slowly. The suspension was centrifuged immediately as described above, and the supernatant was removed completely. The cell pellet was loosened gently, suspended in 1 ml of 75 mM KCl and 2 mM $CaCl_2$ at 4° C., followed by addition of 1 ml of 75 mM KCl, 2 mM $CaCl_2$, 0.5% Triton X-100 at 4° C. The suspension was kept on ice for 10 min, then Dounce homogenized (loose fitting pestle, 5 times, at 4° C.). To the suspension, 1.5 volume of 5% PFA in PBS was added, and incubated 10 min at room temperature with occasional gentle shaking. After incubation, 1/10 volume of 1 M Tris-HCl (pH 7.4) containing 1% BSA was added and further incubated for 10 min at room temperature with gentle shaking. The fixed nuclei were washed twice with PBS containing 1% FCS and stored at 4° C. up to one week. Before FISH hybridization, the fixed nuclei were sedimented by cytospin onto poly L-lysine coated glass slides (Matsunami Glass Ind., Ltd., Japan). Slides were treated with RNAse A (Sigma, 100 µg/ml in 2×SSC, 37° C. for 60 min), washed once with 2×SSC for 3 min, followed by blocking with 3% BSA in PBS for 30 min at 37° C. Slides were incubated in 50% formamide dissolved in 2×SSC for 30 min at room temperature to enable buffer equilibration, followed by addition of the hybridization mixture containing labeled probe (prepared as for standard FISH (Shimizu, et al. (1996)). The sample was covered by a cover slip, sealed completely with rubber cement, denatured at 85° C., and hybridized using overnight incubation at 37° C. Washing and the detection of the hybridized probe was performed as described previously (Shimizu, et al. (1996)). Images were obtained using a BioRad MRC600 confocal system on a Zeiss Axiovert 135 microscope (for FIG. 6, see below). Most images were obtained using x63 objective (Zeiss, Apochromat, 1.40, oil), and zoom factor 2. The acquired digital images were expressed as pseudocolors, and merged using Adobe Photoshop (Adobe Systems Inc., Mountain View, Calif.).

H. Localizing DMs in Interphase Nuclei

The locations of DMs in confocal nuclear sections were determined by measuring the distance from each of the hybridized signals to the center of the nucleus using the corresponding nuclear diameter as a unit length. Coplanar PI (DNA) and FITC (hybridized signal) images intercepting the center of the nucleus were obtained from randomly chosen nuclei. The digital images were merged using COMOS software (BioRad, Hercules, Calif.). The threshold value for each FITC signal was lowered until each signal, representing the domain of one or more DMs, became a single dot to enable accurate distance measurements. The distances from this dot to the center of the nucleus and the nuclear diameter were determined. The location of each signal in the nucleus was expressed by dividing the former number by the latter number. According to this expression, the center of nucleus is 0, and the outer edge of the nuclear membrane is 1. At the same time, the intensity of each signal was measured using an arbitrary unit scale. These values were determined for every signal in each of the nuclear sections using a minimum of 100 randomly chosen nuclei for each sample. This procedure gives rise to a distribution of DM signals in each 2-dimensional focal plane. The heights and widths of each nucleus were found to be approximately equal, indicating that the fixation procedure preserved a spherical nuclear morphology. It was assumed that the distribution of signals within each nuclear volume should correspond to the number of signals we detected at the corresponding radius in 2D space. The number of signals were corrected at each radial location to represent the number that should be present in the spherical volume corresponding to that radius.

I. Simultaneous Determination of DM Location and DNA Replication Using FISH and BrdU Incorporation Rapidly growing COLO 320DM cultures were pulse-labeled using 10 µM BrdU (Sigma) for 1 hour, followed by immediate cell collection. The isolation of nuclei, fixation by PFA, and FISH using purified micronuclei probes were done as described above. After FISH, BrdU incorporation was determined by incubating the slides with anti-BrdU mouse monoclonal antibody (Pharmingen, San Diego, Calif.) at a final concentration of 10 µg/ml in PBS containing 0.1% BSA. After a 60 min incubation at 37° C., the slides were washed 3-times with PBS for 5 min each. The slides were then treated with rhodamine labeled anti-mouse Ig (Boeringer-Mannheim) at a final concentration of 10 µg/ml in PBS containing 0.1% BSA. The slides were incubated for 60 min at 37° C., and washed with PBS 3 times for 5 min. The nuclei were viewed without counter-staining, using MRC 1024 (BioRad) confocal system equipped to Axiovert 135M microscope (Zeiss), and the acquired digital images were processed as described above.

J. Nuclear Budding During Interphase can Selectively Entrap DMs

The classic mechanism by which acentric chromosome fragments such as DMs are lost from cells involves their enclosure within reforming nuclear membranes subsequent to telophase (see Heddle, et al. (1991) for review). However, there is one report that nuclear anomalies resembling micronuclei can be generated in interphase subsequent to gamma irradiation (Duncan, et al. (1985)). A cell line with amplified c-myc genes was used herein to assess the relative contributions of post-mitotic and interphase mechanisms to DM micronucleation.

A fluorescence in situ hybridization (FISH) analysis of COLO 320DM, a colon cancer cell line of neuroendocrine origin, is shown in FIG. 1. A biotinylated FISH probe specific for the c-myc amplicon in COLO 320 cells was obtained from micronuclei purified from COLO 320DM cells (Shimizu, et al. (1996)). FISH analysis with this probe showed that >95% of the cells in the population contained only DMs, and the remainder contained DMs along with one intrachromosomally amplified region (FIG. 1A arrow). Consistent with a previous report (Levan and Levan (1978)), the DMs in the prometaphase spread (FIG. 1A) do not appear to be distributed randomly since many localize to the periphery of the prometaphase ring. Peripheral nuclear localization was also observed in interphase nuclei using confocal nucroscopy (see below).

Analyses of exponentially growing cultures of COLO 320DM cells consistently revealed interphase nuclei with projections or "bud". Approximately 40 to 80% of the nuclear buds contained highly concentrated DM sequences (FIG. 1, panels B–D show representative buds that contain DMs; panel C shows two micronuclei and one bud). The nuclear bud shown in FIG. 1D is highly enriched for amplified sequences since it contains three clusters that stain with PI (the red signal represents DNA staining as these samples were first treated extensively with RNAse) and each PI positive cluster hybridizes intensely with the micronuclear DNA FISH-probe (FIG. 1D'; merge shown in FIG. 1D"). PI-positive buds were occasionally observed that did not hybridize with the DM probe, suggesting that DNA that does not correspond to DM sequences that can be incorporated into buds. However, buds containing DM sequences that appeared to contain relatively little PI-reactive material that did not hybridize with the FISH probe, suggesting that DNA capture within nuclear buds is highly selective for DMs. The selective inclusion of DMs into buds was also readily apparent when a FISH probe derived from a cosmid containing the c-myc (data not shown), a different fixation method (e.g., paraformaldehyde, see FIG. 6), or an isotonic method for the isolation of the nuclei were used.

K. Nuclear Buds and Micronuclei are Formed During S-phase

The nuclei that produce buds exhibited a morphology typical of an interphase cell, not one in mitosis. The kinetics of formation of micronuclei and nuclear buds were therefore determined to ascertain whether these structures can be generated during S-phase. COLO 320DM cells were synchronized at the G1/S boundary using a two step procedure involving treatment with high thymidine concentration to arrest cells during S-phase, release for 12 hrs to enable progression through and exit from S-phase, and then incubation with the DNA polymerase inhibitor aphidicolin to arrest cells at the beginning of the next S-phase (Stein, et al. (1994)). Removal of aphidicolin resulted in rapid entry into S-phase with a peak of DNA synthesis at 4 hrs and a peak of mitosis at 10 hrs (FIG. 2A). The cells entered a second less synchronous cycle up to 19 hrs after release.

The frequencies of micronuclei and buds were ascertained using the DNA specific dye 4',6-diamidino-2-phenylindole (DAPI) (FIGS. 2C and 2D). All samples were hybridized with the DM-painting probe obtained from micronuclei to determine whether these structures contain amplified sequences.

The frequency of nuclei with buds at the G1/S boundary (i.e., t=0) was nearly zero, increased dramatically as the cells progressed through early S-phase (t=0–5 hrs), declined in later S-phase, and then gradually increased as the cells entered and progressed through a second S-phase (FIG. 2C). FISH analysis demonstrated that the buds contain DMs (FIG. 2E). Importantly, the number of total micronuclei, or those with DMs, increased and declined in register with the nuclear buds (FIG. 2C).

Nuclear buds and micronuclei can arise de novo during S-phase progression, and that transit through M-phase is not required for their genesis.

Figure 3A:
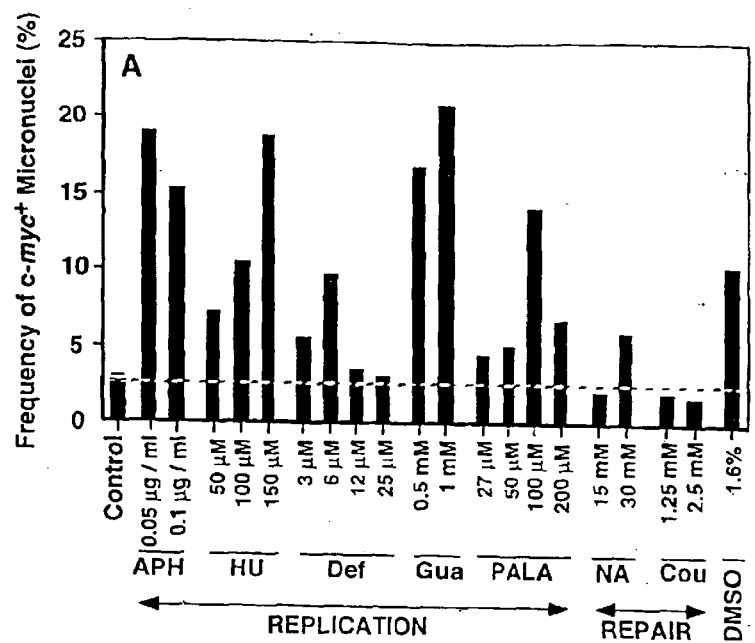
FIGS. 3A and 3B show the effects of various drugs on induction of micronuclei and cell cycle distribution. COLO 320DM cells were treated for 3 days with inhibitors of DNA replication (aphidicolin ("APH"); deferoxamine ("Def"), guanazole ("Gua"); hydroxyurea ("HU"); and PALA), repair (coumarin ("Cou"); nicotinamide ("NA")) or the membrane active agent DMSO at the concentrations indicated.
Figure 3B:
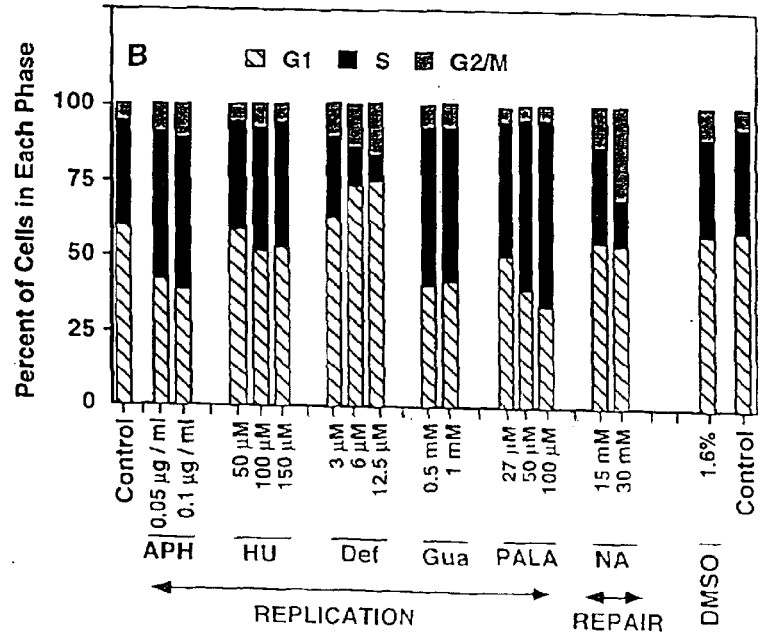

The kinetic and nuclear morphologic analyses of budding and micronucleation indicate that both events can occur during S-phase. Since slowing replication fork progression can lead to DNA breakage (Eki, et al. (1987) and Linke, et al. (1996)), and micronuclei preferentially capture acentric fragments (Von Hoff, et al. (1992) and Shimizu, et al. (1996)), whether such inhibitors increase S-phase micronucleation efficiency was determined. The drugs tested included inhibitors of ribonucleotide reductase (HU, deferoxamine, guanazole), an inhibitor of the CAD enzyme complex that catalyzes the first three steps of de novo pyrimidine biosynthesis (PALA), and aphidicolin. DNA synthesis inhibitors produced substantial increases in micronucleation, and this generally correlated with an increased fraction of cells in S-phase (FIGS. 3A and 3B). A sharp decrease in micronucleation efficiency was observed for deferoxamine and PALA when these drugs were used at concentrations that severely inhibited S-phase (FIG. 3B). These data indicate that micronucleation can result from inhibitors that retard replication fork progression and lengthen S-phase.

The effects of inhibitors were analyzed that do not affect DNA synthesis to ascertain whether micronucleation can result from interfering with other DNA transactions such as DNA repair, or by interfering with membrane structure. Two inhibitors of poly (ADP-ribose) polymerase (nicotinamide and coumarin) were tested since ADP ribosylation has been implicated in DNA repair (Satoh and Lindahl (1992)), and inhibiting repair could increase the probability of generating acentric chromosome fragments. The effects of DMSO, a membrane-active polar compound previously reported to reduce DM copy number in some tumor cell lines (Shima, et al. (1989) and Eckhardt, et al. (1994)) were tested. DMSO increased micronucleation without lengthening S-phase (FIGS. 3A and 3B). Coumarin had no effect on micronucleation, while nicotinamide produced a small increase under conditions that apparently increased the amount of damage in the cells as there was a significant increase in the G2 fraction (FIGS. 3A and 3B). These data are consistent with the view that micronucleation efficiency can be increased by at least two mechanisms, one of which presumably involves perturbing replication fork progression and another of which may involve events occurring outside of S-phase.

L. Peripheral Nuclear Localization of DMs Correlates with Their Elimination by Budding Insight into the mechanisms underlying the selective inclusion of DMs into nuclear buds and the formation of these structures in interphase was obtained by confocal microscopy. PFA-fixation of nuclei was used for optimal preservation of nuclear morphology (Manuelidis and Borden (1988)).

Figures 4A, 4B, 4C, 4D, 4E, 4F:
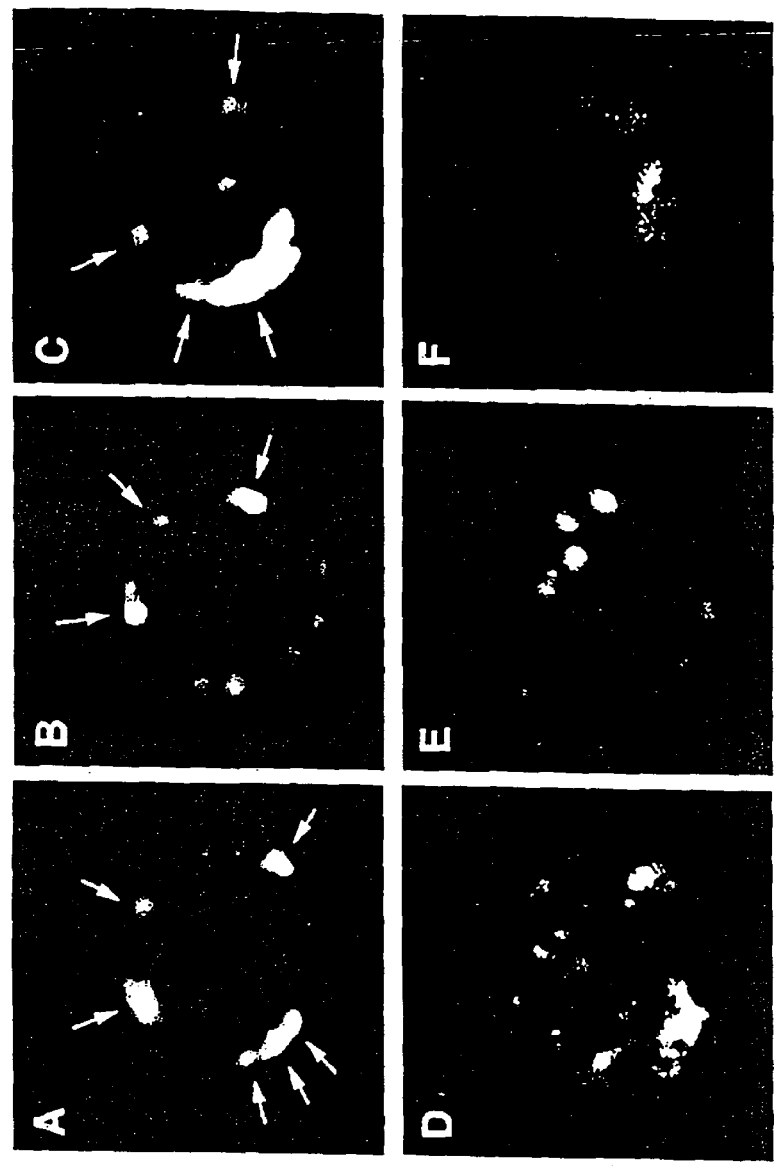
FIGS. 4A through 4F show localization of DMs in interphase COLO 320DM nuclei. PFA-fixed isolated nuclei from a culture of COLO 320DM cells were hybridized with a DM-painting probe, then counterstained with PI. Optical sections near the center of each nucleus were obtained using confocal laser scanning microscopy. Each of three representative images of nuclei from the rapidly growing culture (see FIGS. 4A to 4C) and from a culture treated with 100 μM hydroxyurea for 3 days (see FIGS. 4D to 4F) are shown. In untreated cultures, DMs preferentially located just beneath the nuclear membrane as indicated by the arrows. Very few peripheral DMs were detected in the nuclei from the HU treated culture, and most of the signals localized well within the nucleus as shown.
Figures 5A, 5B, 5C:
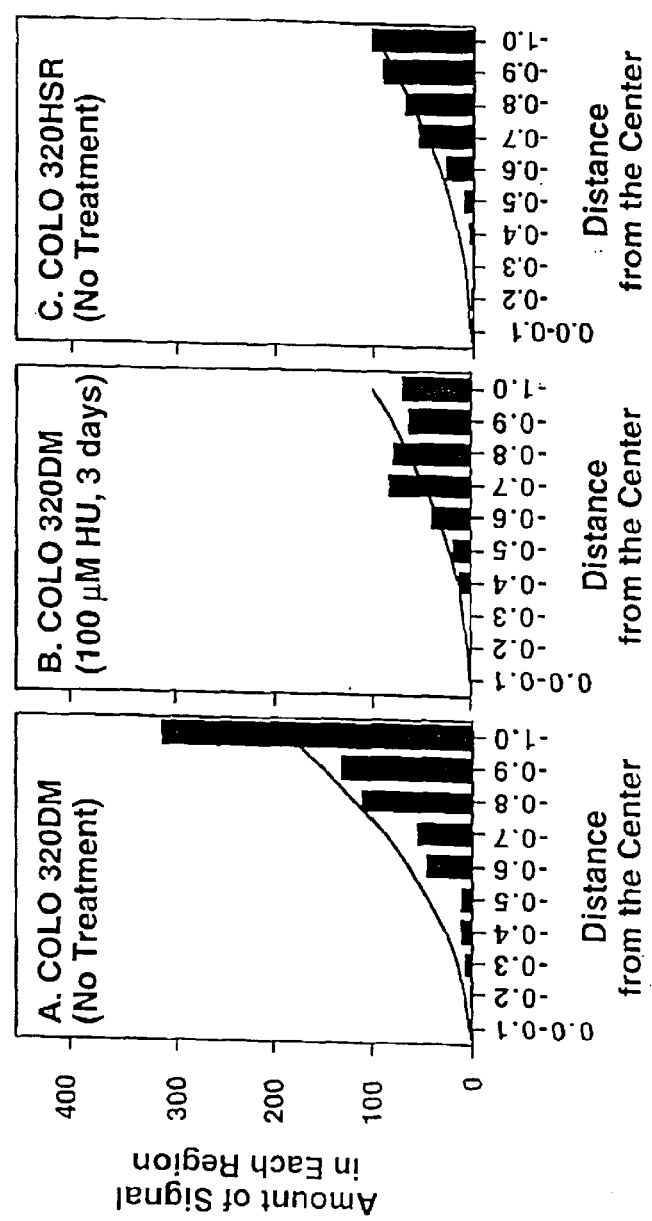
FIGS. 5A through 5C show quantitative analysis of the nuclear positions of DMs and chromosomally amplified sequences. The nuclei from a rapidly growing culture of COLO 320DM cells (see FIG. 5A), COLO 320DM treated with 100 μM HU for 3 days (see FIG. 5B), and rapidly growing COLO 320 cells with chromosomally amplified c-myc sequences (COLO 320HSR) (see FIG. 5C) were hybridized with a probe for the c-myc amplicon. Sections intercepting the center of each nucleus were obtained as in FIG. 4. For each section, the position and intensity of each hybridized signal was measured. Each analysis represents measurements on 100 randomly chosen nuclei. The abscissa depicts the fractional distance from the nuclear center (0 is the center and 1 is the periphery), and the ordinate is the number of signals detected at each position in 100 nuclei. The theoretical random distribution curves based on signals per nuclear volume at each position are shown in each graph as explained in greater detail below.

Confocal sections from three representative nuclei isolated from rapidly growing untreated COLO 320DM cells are shown in FIGS. 4A–C. FISH revealed preferential localization of most DM sequences to the nuclear periphery, as indicated by the significant hybridization intensity, clustering and number of DM signals at the extreme edge of each nucleus. Note the substantial deviation from a random distribution of DM sequences at the nuclear periphery (quantified in FIG. 5A by measuring DM positions relative to the center of each nucleus in 100 interphase nuclei). By contrast, sequences amplified within chromosomes in the closely related cell line COLO 320HSR showed a nearly random distribution throughout the nucleus (FIG. 5C). HU treatment preferentially depleted DMs from the nuclear periphery (FIGS. 4D–F with quantification in FIG. 5B) and reduced the DM content per cell by approximately 3-fold as determined by competitive PCR amplification (see Shimizu, et al. (1996) for method; data not shown). Taken together with the data above, these results indicate that DM sequences located at the nuclear periphery are preferentially incorporated into nuclear buds, which are then removed from the nucleus through the formation of micronuclei.

M. Incorporation of Replicating DM Sequences into Nuclear Buds

The correlation between S-phase progression, nuclear budding and micronucleation reported above led the inventors to investigate whether DM sequences undergoing replication are targeted for inclusion into buds. Pulse-labeling COLO 320DM cells with BrdU, and then hybridizing the isolated nuclei with the DM FISH probe. Subsequent reaction with an anti-BrdU antibody and fluorescein labeled secondary antibody enabled simultaneous detection of nuclei, buds and micronuclei containing DMs that were undergoing DNA replication during the brief labeling interval. FISH analysis of two representative confocal sections (FIGS. 6A–A", B–B") shows that nuclear buds in these cells (arrows) contain highly concentrated DM-sequences. The nuclei, nuclear buds and peripheral regions of each nucleus incorporated BrdU, indicating that these buds were formed in nuclei that were synthesizing DNA at the time of bud formation. Table 1 shows that BrdU+, DM+ buds (type 1, 1') represent 48% of the total population of DM containing buds. Some nuclei incorporated BrdU, but the buds they produced were not labeled (type 2, 2'; 35%). Some of these buds were also generated during S-phase (as opposed to during the previous cycle), and that they did not reveal BrdU incorporation because their DNA was not undergoing replication during the brief BrdU incubation period.

Figures 6A, 6B, 6C:
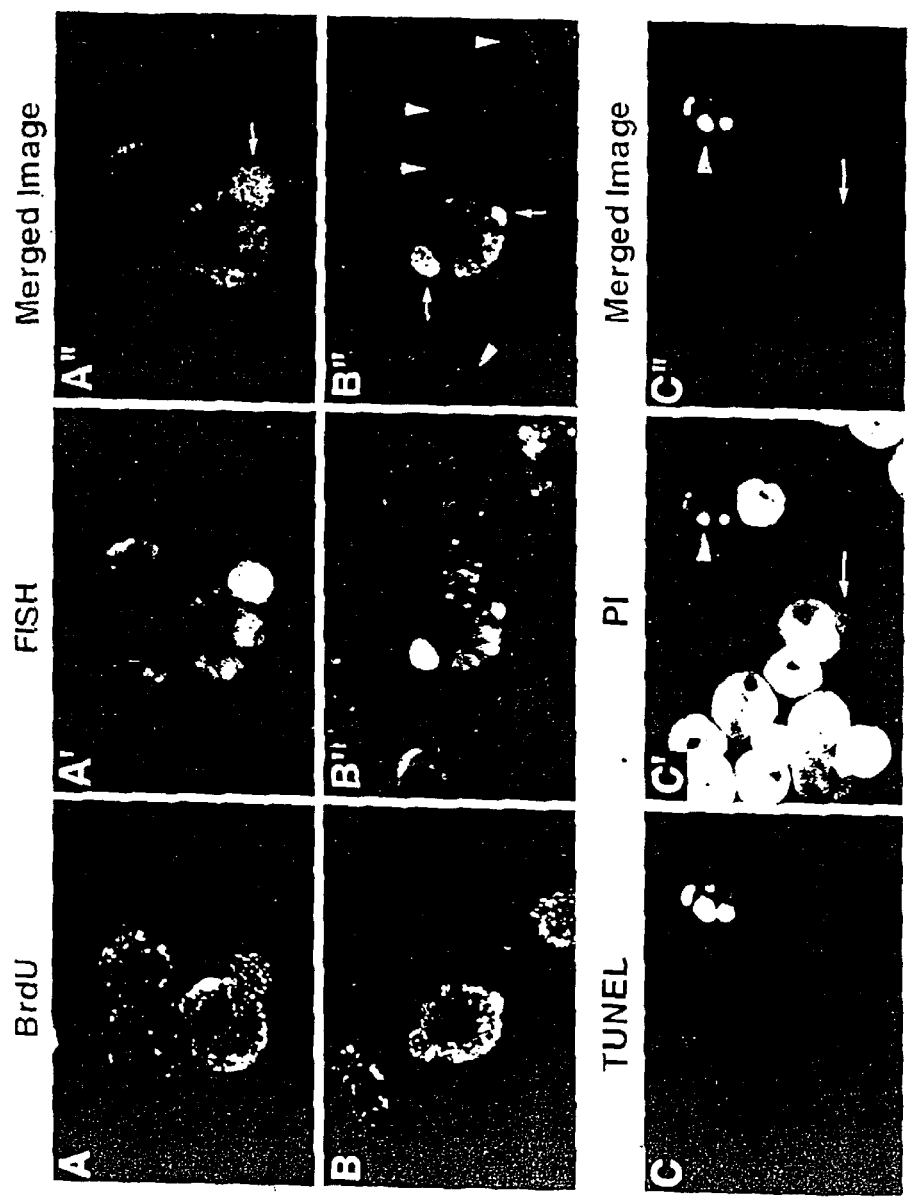
FIGS. 6A through 6C show the analyses of DM DNA replication and apoptosis in COLO-320DM cells.

The S-phase micronucleation process described here superficially resembles the induction of "nuclear anomalies" by an apoptotic mechanism following gamma-irradiation (Duncan, et al. (1985)) or colchicine-treatment (Duncan and Heddle (1984)). However, the absence of highly condensed DNA in the nuclei producing buds suggests that they were not undergoing apoptosis at the time of bud formation. In order to determine whether budding and micronucleation are separable from apoptosis, it was determined whether buds contain the condensed, fragmented DNA that typifies apoptotic cells. Fragmented DNA was detected using the TUNEL assay in which terminal transferase is employed to add BrdU to the 3'-OH groups generated by apoptotic DNA fragmentation (Gavrieli, et al. (1992)). The cells were also stained with PI to visualize all nuclei and buds. An example of the data obtained from such an analysis of COLO 320DM cells is shown in FIGS. 6C–C". The TUNEL assay shows one cell with a lobular nucleus that exhibits a strong TUNEL reaction and typifies the fragmented, condensed DNA observed in apoptotic nuclei (Cohen (1993)). The PI staining in the middle panel reveals a cell producing a nuclear bud that does not stain by the TUNEL assay and does not exhibit the pycnotic structure of the apoptotic nucleus. Synchronization experiments showed that while approximately 5% of cells generated buds at the peak of S-phase (e.g., see FIG. 2C), only 0.5–1% were TUNEL positive.

N. Micronucleation Occurs Infrequently in Normal Cells, and is Increased Upon p53 Inactivation Micronucleation occurs at significantly lower rates in normal cells than tumor cell lines (Roser, et al. (1989) and Bondy, et al. (1993)). Since micronucleation can be induced by chromosome breakage (Heddle and Carrano (1977)), the observed increase in micronucleation in tumor cells might result from mutations that increase the probability of DNA breakage. The tumor suppressor p53 controls G1 checkpoints activated by DNA breakage and rNTP depletion induced by PALA treatment, and DNA breakage can occur in p53-deficient cell lines that enter S-phase during PALA treatment (Livingstone, et al. (1992); Yin, et al. (1992) and Linke, et al. (1996)). As reported above, PALA also induces S-phase micronucleation in COLO 320 cells. These data led us to investigate whether p53 inactivation in normal diploid fibroblasts results in increased S-phase budding and micronucleation.

Human WS1 normal diploid fibroblasts and two nearly isogenic derivatives generated by retroviral transduction of the neomycin phosphotransferase gene (WS1-neo) or an oncogenic derivative of the human papilloma virus E6 gene (WS1-E6) were used. The E6 gene product facilitates p53 degradation by a ubiquitin dependent pathway (Scheffner, et al. (1990) and Crook, et al. (1991)). Cell cycle checkpoint controls that regulate entry into S-phase in the presence of DNA damage or limiting rNTP concentrations appear to be inactivated to equivalent degrees in human cells expressing mutant p53, oncogenic E6 protein, and mouse embryo fibroblasts with homozygous p53 knock out (Kastan, et al. (1992); Kuerbitz, et al. (1992); Livingstone, et al. (1992); Yin, et al. (1992); White, et al. (1994); Linke, et al. (1996) and Linke, et al. (1997)). It was previously shown that the frequency of gamma-radiation induced micronucleation is higher in p53-/- MEFs than in wild type MEFs (Huang, et al. (1996)). It is likely, therefore, that effects on micronucleation observed upon expression of oncogenic E6 protein relate to inactivation of p53 rather than to other proteins that may be affected by E6.

Figures 7A, 7B, 7C, 7D:
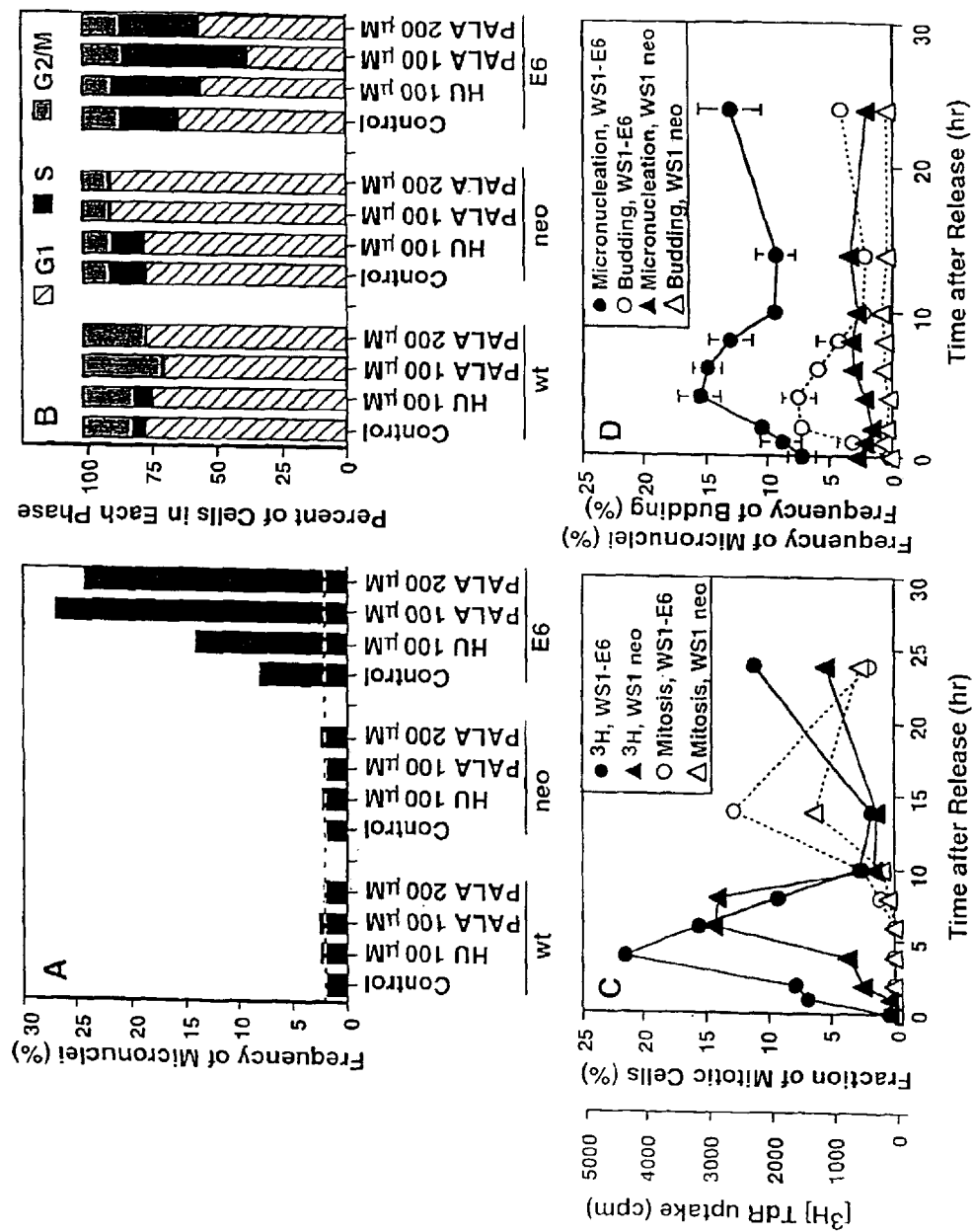
FIGS. 7A through 7D show that p53 deficiency increases S-phase budding and micronucleation in normal human diploid fibroblasts. Wild type (wt) WS1 human diploid fibroblasts, or transformants expressing the neomycin resistance gene (neo) or both neo and the human papilloma virus E6 protein (E6) were generated by retroviral transduction. These cells were cultured in the absence or the presence of HU or PALA at the indicated concentrations for 3 days.

The data shown in FIG. 7 demonstrate that E6 gene expression increases the micronucleation rate of WS1 cells. WS1 cells exhibit a low micronucleation rate that is not increased by HU or PALA (FIG. 7A). Consistent with previous studies (Linke, et al. (1996)), PALA induced a G1 cell cycle arrest, while HU did not significantly affect the percentage of WS1 cells in S-phase at the concentration employed (FIG. 7B). By contrast, E6 expression increased the micronucleation efficiency of these fibroblasts growing under normal conditions, and both HU and PALA produced a substantial further increase in micronucleation rate (FIG. 7A), which correlated with a significant increase in the number of cells in S-phase (FIG. 7B). The importance of an E6 target, it was inferred to be p53, in limiting micronucleation is evident in other cell types since similar results were obtained using normal retinal pigmented epithelial cells (RPE-h) and their E6 expressing derivatives.

The elongation of S-phase and induction of micronuclei by HU and PALA in both COLO 320DM and WS1 E6 cells led us to assess whether budding in S-phase is the predominant mechanism of micronucleation in WS1-E6 cells. WS1-neo and WS1-E6 cells were arrested in G0 by serum deprivation, and then released in the presence of aphidicolin to arrest the cells at the G1/S boundary (FIG. 7C). Synchronization by serum depletion did not increase micronucleation rate and the micronucleation and budding frequencies did not increase in S-phase in WS1-neo cells (FIG. 7D). By contrast, removal of aphidicolin from WS1-E6 cells resulted in significant increases in the frequencies of both nuclear budding and micronucleation as the cells progressed through S-phase (FIG. 7D). Since DNA damage does not induce apoptosis in either WS1 or WS1-E6 cells (Di Leonardo, et al. (1994); Linke, et al. (1996) and Linke, et al. (1997)), the increased S-phase micronucleation observed in these cells occurs independent of an apoptotic program.

O. S-phase Budding and Micronucleation do not Require Prior Engagement of an Apoptotic Program; but can Result in Apoptosis Apoptosis can generate nuclear blebs (Dini, et al. (1996)) and has been inferred to produce "nuclear anomalies" that resemble micronuclei (Duncan and Heddle (1984) and Duncan, et al. (1985)). However, the analyses reported herein show that nuclei that produced buds were not pycnotic and fragmented like apoptotic nuclei. Buds and micronuclei generated in COLO 320DM cells within a single S-phase were not TUNEL positive, indicating that they did not contain fragmented DNA. While apoptotic cells did arise in HU treated COLO 320DM cultures, this required prolonged incubation, and occurred after a substantial fraction of the amplified c-myc genes had been removed. Furthermore, cells undergoing budding and micronucleation survived for several days, which is not expected if an apoptotic program were activated prior to micronucleation. A time course experiment similar to that described above (e.g., FIG. 2) revealed that budding increases during a single S-phase while the fraction of cells undergoing apoptosis remained roughly constant, and that most of those generating buds were not TUNEL positive. Finally, though it was not observed apoptosis in normal fibroblasts (Di Leonardo et al. (1994)), and loss of p53 function typically makes cells more resistant to apoptosis induced by growth conditions that can lead to DNA damage (White (1994)), S-phase budding and micronucleation were induced in normal diploid fibroblasts upon expression of oncogenic papillomavirus E6 protein, presumably due to elimination of p53 function.

TABLE 1

Quantification of budding and micronucleation

| Type | BrdU labeling in: | | Frequency of DM+Buds that belong to each type |
|---|---|---|---|
| | DM+buds | Nuclei | |
| 1 | + | + | 26/60 (43%) |
| 1' | ± | + | 3/60 (5%) |
| 2 | − | + | 9/60 (15%) |
| 2' | − | ± | 12/60 (20%) |
| 3 | − | − | 10/60 (17%) |

Nuclei from COLO 320DM were pulse-labeled with BrdU, and then analyzed for BrdU incorporation and DMs as described in FIG. 6. Nuclei were observed using epifluorescence microscopy. Sixty nuclei with DM+buds were classified according to whether they labeled with BrdU (classes 1, 1'), whether the nuclei to which they were attached labeled with BrdU (classes 2, 2'), or whether neither bud nor nucleus labeled with BrdU (class 3). The number of nuclei belonging to each were scored and expressed as nuclei in that class/total number scored.

In sum, circular, autonomously replicating DNA fragments such as double minute chromosomes (DMs) are generated in many cancer cells (Barker (1982); Cowell (1982) and Benner, et al. (1991)). These structures encode proteins that provide survival advantages in vivo, or resistance to a variety of chemotherapeutic agents. In the S-phase budding mechanism, DMs are preferentially located at the periphery of the interphase nucleus, and selectively encapsulated into nuclear buds which then pinch off to form micronuclei during DNA replication. This process is an alternative to the classical post-mitotic mechanism of generating micronuclei. Decrease in DM content can be achieved by either expulsion of micronuclei containing DMs from the cell, or by degradation of DM DNA within intracellular micronuclei. In either case, loss of DM sequences from the nucleus results in reversion of the tumor phenotype, differentiation, or apoptosis.

II. Detection and Analysis of Chromosomal and Extrachromosomal DNA

A. Construction of H2B-GFP Expression Vector

Human H2B gene was amplified by PCR from human placental genomic DNA using primers which introduce KpnI and BamHI sites at the ends of H2B sequence (Zhong, et al. (1983)).

Primer 1: 5'-CGGGTACCGCCACCATGCCAGAG CCAGCGAAGTCTGCT-3'

Primer 2: 5'-CGGGATCCTTAGCGCTGGTGTACTTGG TGAC-3'

Primer 1 introduces the Kozak consensus sequence in front of the initiation codon. PCR reaction parameters were as follows: 95° C. for 10 min, cycles at 94° C. for 1 min, 50° C. for 1 min, 72° C. for 2 min, followed by 72° C. for 5 min. The PCR product was digested with KpnI and BamHI and the digested fragment was subcloned into pEGFPN1 or pEGFPC1 vector (Clontech, Palo Alto, Calif.) (Yang, et al. (1996)) digested with KpnI and BamHI, to make C-terminally tagged H2B and N-terminally tagged H2B, respectively. CMV promoters of these vectors were replaced with EF1α promoter, a strong promoter in mammalian cells (Mizushima and Nagata (1990)). H2B-GFP expression cassettes driven by EF1α promoter were subcloned into the backbone vector with the blasticidin S-resistance gene (Izumi, et al. (1991)) which is driven by SRα promoter (Takebe, et al. (1988)).

B. Cell Lines and Transfection

HeLa cells were grown as monolayers in DMEM medium supplemented with 10% FCS. Subconfluent cells were transfected with 20 µg of H2B-GFP expression vectors (either H2B-G or G-H2B) using a modified calcium phosphate precipitation protocol (Chen, et al. (1987)). Transfected cells were replated 48 hrs after transfection and 5 µg/ml blasticidin-S (Calbiochem, La Jolla, Calif.) was added 72 hrs after transfection. After five days, the medium was changed to 2 µg/ml blasticidin-S. After 15 days of drug selection, surviving colonies were checked under fluorescent microscopy and GFP-positive colonies were isolated. Several clones were selected and expanded into cell lines for further analyses.

C. Mononucleosome Preparation

Mononucleosomes were purified as previously described (Dubochet and Noll (1978) and Laybourn and Kadonaga (1991)) with minor modifications. HeLa cells and stable cells expressing H2B-GFP ($3 \times 10^7$) were trypsinized, harvested and washed once with 1×RSB buffer (10 mM Tris pH 7.6, 15 mM NaCl, 1.5 mm $MgCl_2$). After centrifugation, cell pellet was resuspended in 1×RSB buffer with 1% Triton-X 100, homogenized 5 strokes with loose-fitting pestle to release nuclei. Nuclei were collected by centrifugation and washed twice with 1 ml of buffer A (15 mM Tris pH 7.5, 15 mM NaCl, 60 mM KCl, 0.34 M sucrose, 0.5 mM spermidine, 0.15 mM spermine, 0.25 mM PMSF and 0.1% B-mercaptoethanol). Nuclei were finally resuspended in 1 ml of buffer A and 10 µl of 0.1 M $CaCl_2$ was added.

For making nucleosomal ladder, suspended nuclei was digested by adding 2 µl of Micrococcal nuclease (Sigma, 200 units/ml) (final concentration is 0.4 units/ml buffer A) for 1, 5, 10, 15, 30, and 60 min at 37° C. Hundred µl of aliquots were taken at each time point and 2.5 µl of 0.5 M EDTA was added to stop the reaction. Thirty µl $dH_2O$), 20 µl 10% SDS, and 40 µl 5M NaCl were added to each tube. The mixtures were extracted with phenol/chloroform and 5 µl of supernatant was analyzed by 1.5% agarose gel electrophoresis.

Limit digests for making mononucleosomes were performed by adding 15 µl of micrococcal nuclease (200 units/ml) to 1.5 ml of suspended nuclei in buffer A (final concentration is 2 units/ml buffer A). After 2 hr digestion at 37° C., 30 µl of 0.5 M EDTA was added to stop the reaction. The digest was centrifuged 10000 rpm for 10 min and supernatant was removed. The pellet was resuspended in 450 µl of 10 mM EDTA and 50 µl of 5M NaCl was added to solubilize chromatin. After 14000 rpm centrifigation for 5 min, the supernatant was fractionated on a 5–30% sucrose gradient for 18 hr at 26K rpm in a Beckman SW41 rotor. After centrifugation, 1 ml fractions were collected and small aliquots (50 µl) of samples were taken for DNA analyses. The rest of the samples (950 µl) were precipitated with 280 µl of 100% TCA with deoxycholic acid and left on ice for 10 min. The samples were then centrifuged 3000 rpm for 5 min and pellet was washed with acetone followed by 70% cold ethanol wash. The pellet was air dried and resuspended in 20 µl of 1×SDS sample buffer and analyzed by 15% SDS-PAGE and Coomassie staining. The same aliquots of the samples were analyzed by 15% SDS-PAGE and Western blotting was performed with anti human H2B antibody (Chemicon) as a primary antibody and horse radish peroxidase conjugated anti rabbit IgG as a secondary antibody.

Signals were detected by enhanced luminol reagent (NEN Life Science Products) according to manufacturer's instructions.

D. FACS Analyses

HeLa cells and HeLa with H2B-GFP expression were harvested by trypsinization, fixed in 70% ethanol for 3 hrs at 4°. Cells were stained with 20 μg/ml propidium iodide (PI) containing RNAse. Fluorescence of cells was measured using a Becton Dickinson FACScan. The red (PI) and green (GFP) emissions from each cell were separated and measured using standard optics of the FACScan. Color compensation was done to eliminate the artifact due to the overlap of PI and GFP emission. Cell debris and fixation artifacts were gated out. Data analysis was done using Cell Quest and G1, S, and G2/M fractions were quantified using Multicycle.

E. Fluorescence Microscopy

Chromosome spreads: HeLa cells expressing H2B-GFP were treated with colcemid for 60 min, trypsinized, harvested, and resuspended in hypotonic buffer (10 mM Tris pH 7.4, 10 mM NaCl, 5 mM MgCl2) (1.5×106 cells/ml) for 10 min. Fifty μl of swollen cells were attached to the poly L-lysine coated slide glasses by cytospin (90 sec), fixed by 3.7% formaldehyde for 5 min, 0.1% NP40 in PBS- for 10 min, and counter-stained with DAPI (1 μg/ml). Images were collected with Nikon fluorescent microscope equipped with either DAPI (excitation 360 nm/emission 460 nm) or FITC (excitation 460 nm/emission 535 nm) filter set.

Immunofluorescence: Cells were grown on 12 mm coverslips and were processed for immunofluorescence with a human anticentromere antiserum as described previously (Sullivan et al. (1994)). Briefly, cells were fixed with 4% formaldehyde in PBS, blocked with 1% BSA in PBS with 0.1% Triton-X100 (PBS-TX-BSA). Primary antibody was diluted 1:2000 in PBS-TX-BSA, applied to the coverslips and incubated at 37° C. for 30 minutes. Coverslips were washed 4 times in PBS-TX for 4 minutes each and then incubated with rhodamine-coupled sheep anti-human IgG (Southern Biotechnologies, Birmingham, Ala.) at a 1:200 dilution in PBS-TX-BSA. Coverslips were incubated for 30 minutes at 37° C., washed 4 times then rinsed in distilled water and allowed to air dry. They were then mounted on slides with Slow Fade (Molecular Probes, Eugene, Oreg.). Microscopy was performed on a BioRad 1024 confocal microscope built on a Zeiss Axiovert 100 using a 63×1.4 NA Zeiss Plan Achromat objective lens.

Live cells: Cells were grown up on 25 mm coverslips and mounted with prewarmed culture medium in a Dvorak-Stotler chamber (Nicholson Precision Instruments, Gaithersburg, Md.). Images were collected, on the BioRad 1024 confocal microscope described above using either the 63× lens or a 40×1.3 NA Neofluar objective using a laser power of 0.3–1% for GFP fluorescence. Transmitted light images were collected with DIC optics. Fluorescence images were overlaid onto DIC images using Adobe Photoshop.

F. Chromosome Labeling by H2B-GFP

Living cells with H2B-GFP expression were observed by confocal microscopy to determine the pattern of chromatin staining in interphase and mitotic cells. As shown in FIG. 12, H2B-GFP enabled highly sensitive chromatin detection in all phases of the cell cycle. Fixation and permeabilization of the cells, which might cause artificial distortion of intracellular structure, is not required to obtain such images. H2B-GFP is highly specific for nuclear chromatin since no fluorescence was observed in the cytoplasm. In addition, H2B-GFP provides a remarkable level of sensitivity. For example, a lagging sister chromatid which was approaching the metaphase plate was clearly observed. The heterogeneity of chromatin distribution was indicated by variable fluorescence intensity in the interphase nucleus. The fine intra-nuclear chromatin architecture visualized by H2B-GFP is consistent with the previously-reported deconvoluted optical sectioning images obtained by 4'6-diamidinophenylindole (DAPI) staining (Belmont, et al. (1994)). Chromosome spreads of the H2B-GFP expressing cells also show identical staining patterns between GFP and DAPI (FIG. 12E).

Figures 12A, 12B, 12C, 12D:
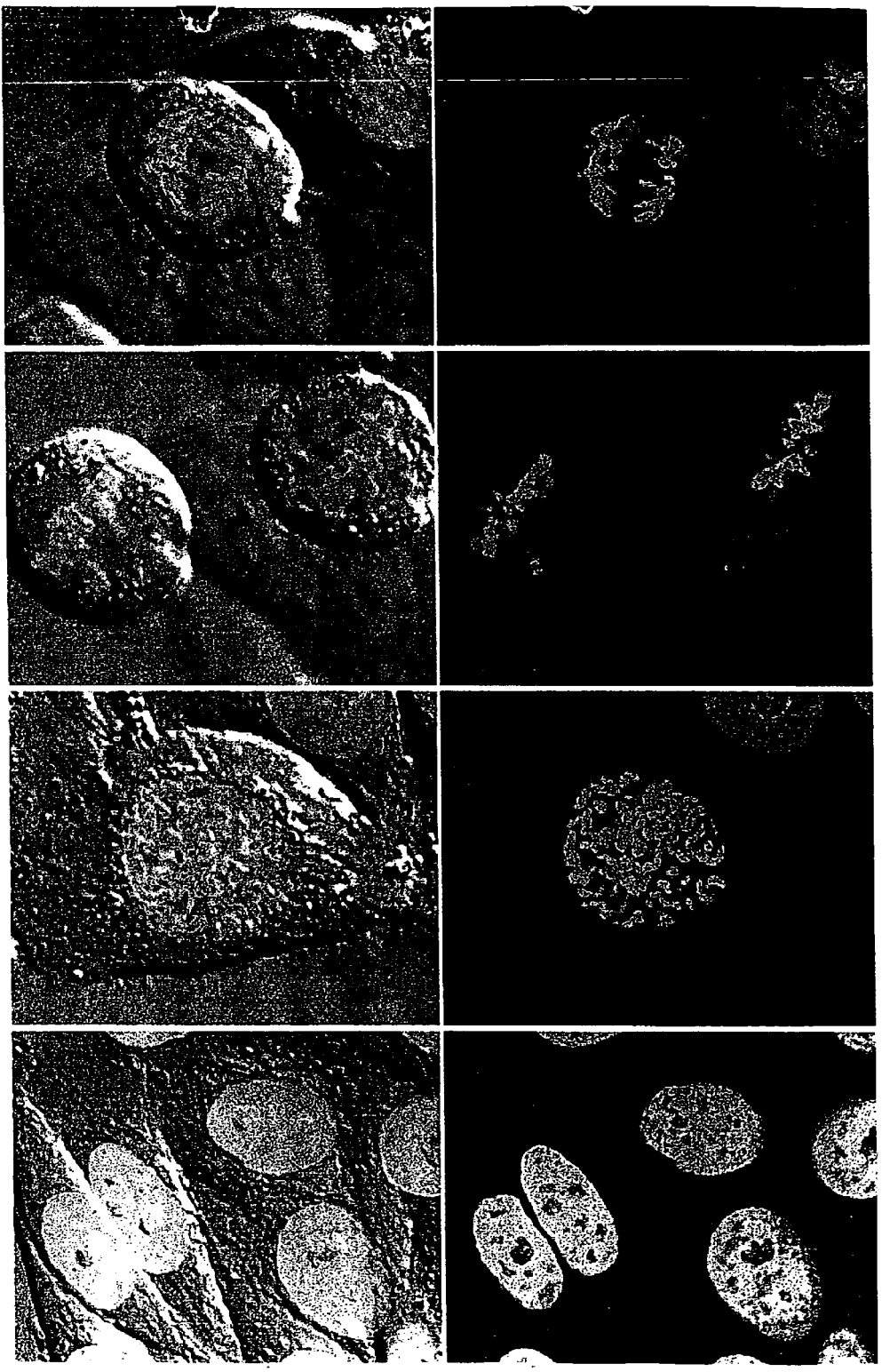
FIGS. 12A through 12E show localization of H2B-GFP protein. Confocal microscopic images of various stages of the live HeLa cells expressing H2B-GFP. Interphase (FIG. 12A), prophase (FIG. 12B), metaphase (FIG. 12C), and anaphase (FIG. 12D) cells are shown. In each panel, the GFP signal is shown in green at left and with a reflectance mode image on the right.
Figure 12E:
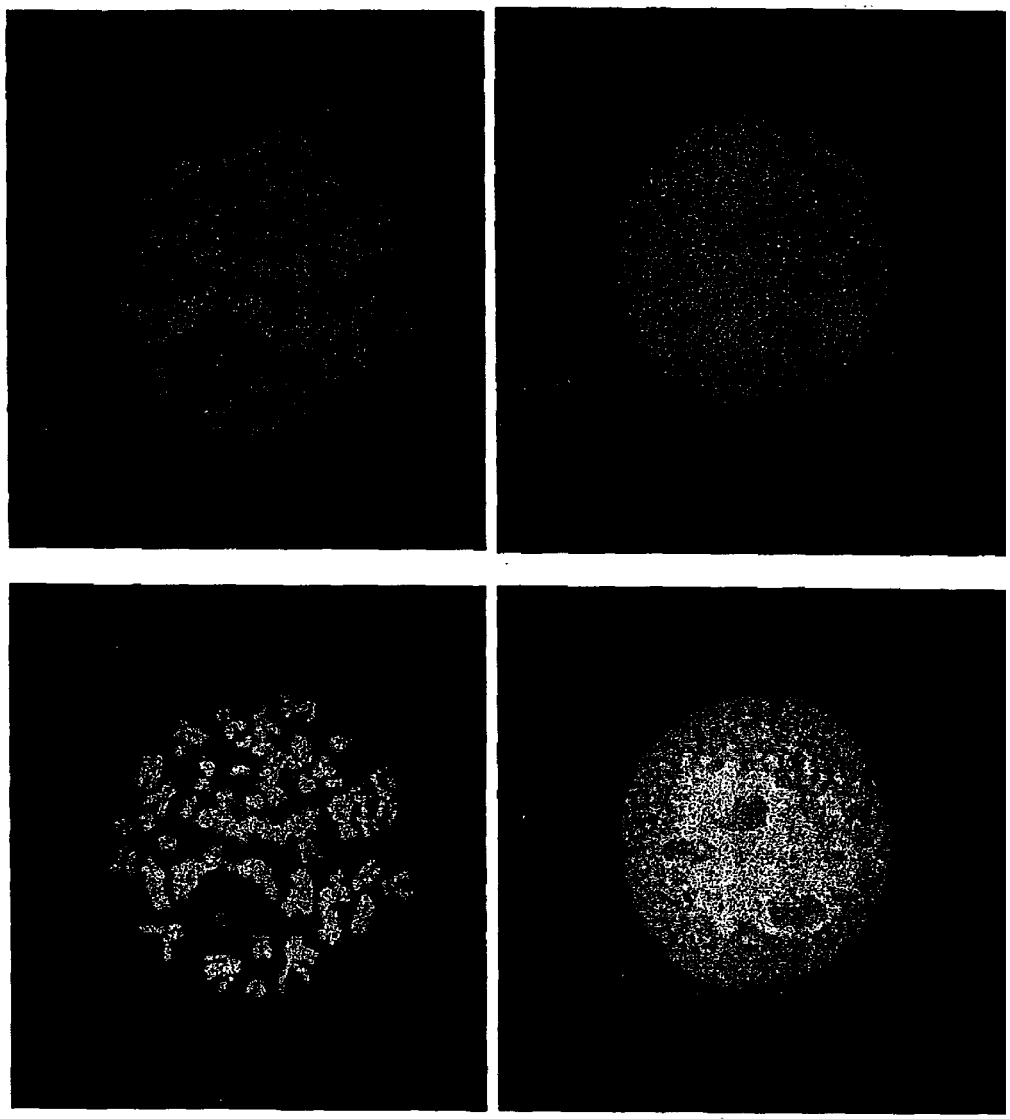

In some interpose nuclei, dense GFP staining was observed at perinucleolar regions, suggesting the existence of perinucleolar heterochromatic domains (FIG. 12A). The positions of centromeres to ascertain whether their localization would correspond to the regions heavily stained by H2B-GFP. H2B-GFP expressing cells were fixed and stained with anti-centromere antibodies and observed by confocal microscopy. Many centromeres are located at perinucleolar regions in some interphase nuclei as previously described (Moroi, et al. (1981)). These centromeres overlap with the region that stained densely with H2B-GFP. Other centromeres, not located at the perinucleolar regions, also frequently associated with regions exhibiting dense H2B-GFP staining. Dense H2B-GFP staining regions are also observed at the inner surface of the nuclear envelope, suggesting the existence of peripheral heterochromatin.

G. Visualization of Double Minute Chromosomes in Live Cells

One of the possible applications of H2B-GFP staining should be a detailed analysis of chromosome segregation during mitosis. A retroviral vector was constructed to enable high efficiency transfer and expression of H2B-GFP. A vesicular stomatitis virus G glycoprotein (VSV-G) pseudotyped retroviral vector was constructed and used (see U.S. Pat. No. 5,512,421 and PCT/US95/11892 for construction of the vector), as this system affords the highest viral titers available. COLO 320DM cells harboring DMs with c-myc amplification were infected with the H2B-GFP retrovirus, and 2 days later, nearly 100% of the cells expressed H2B-GFP protein. Using epifluorescence microscopy equipped with CCD camera, DMs were readily observed as small fluorescent dots in mitotic cells.

H. Stable Expression of H2B-GFP in HeLa Cells.

Figure 8:
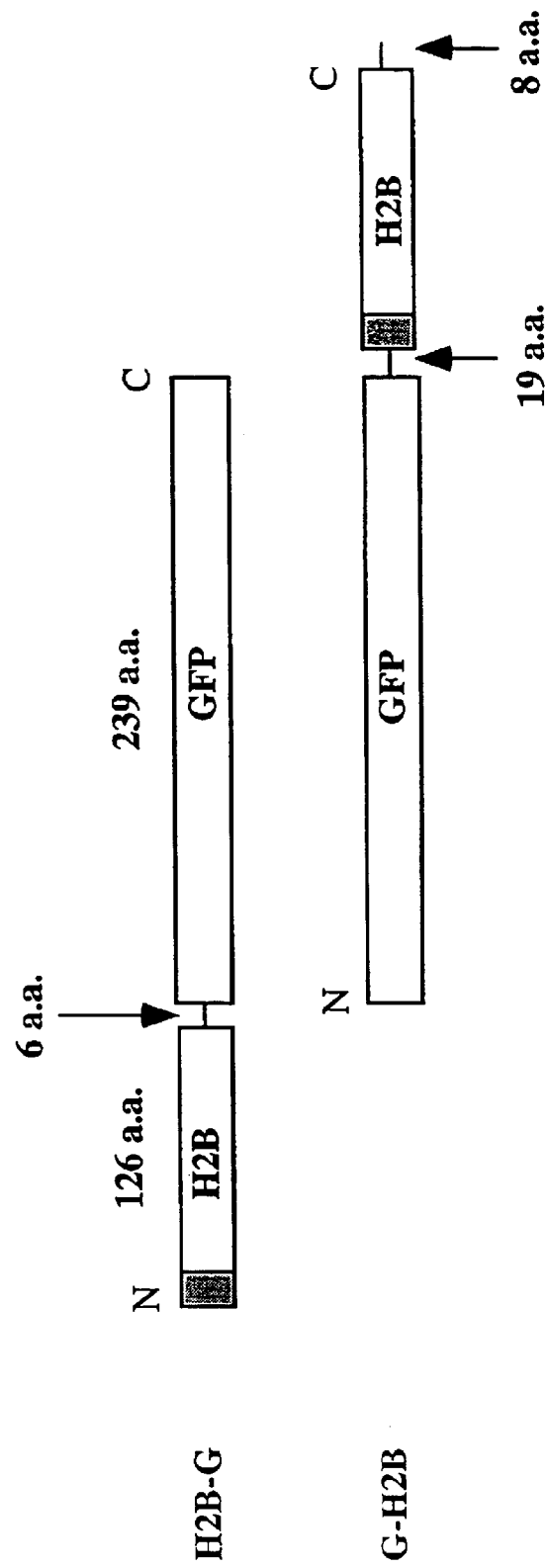
FIG. 8 shows a schematic representation of H2B-GFP chimeric peptides. H2B peptide (239 a.a.) was tagged with GFP peptide (126 a.a.) either at its C-terminal (H2B-G) or its N-terminal (G-H2B). The number of extra amino acids at the junction of H2B and GFP peptides are indicated. Histone N-terminal tails are indicated as shaded boxes.
Figure 9:
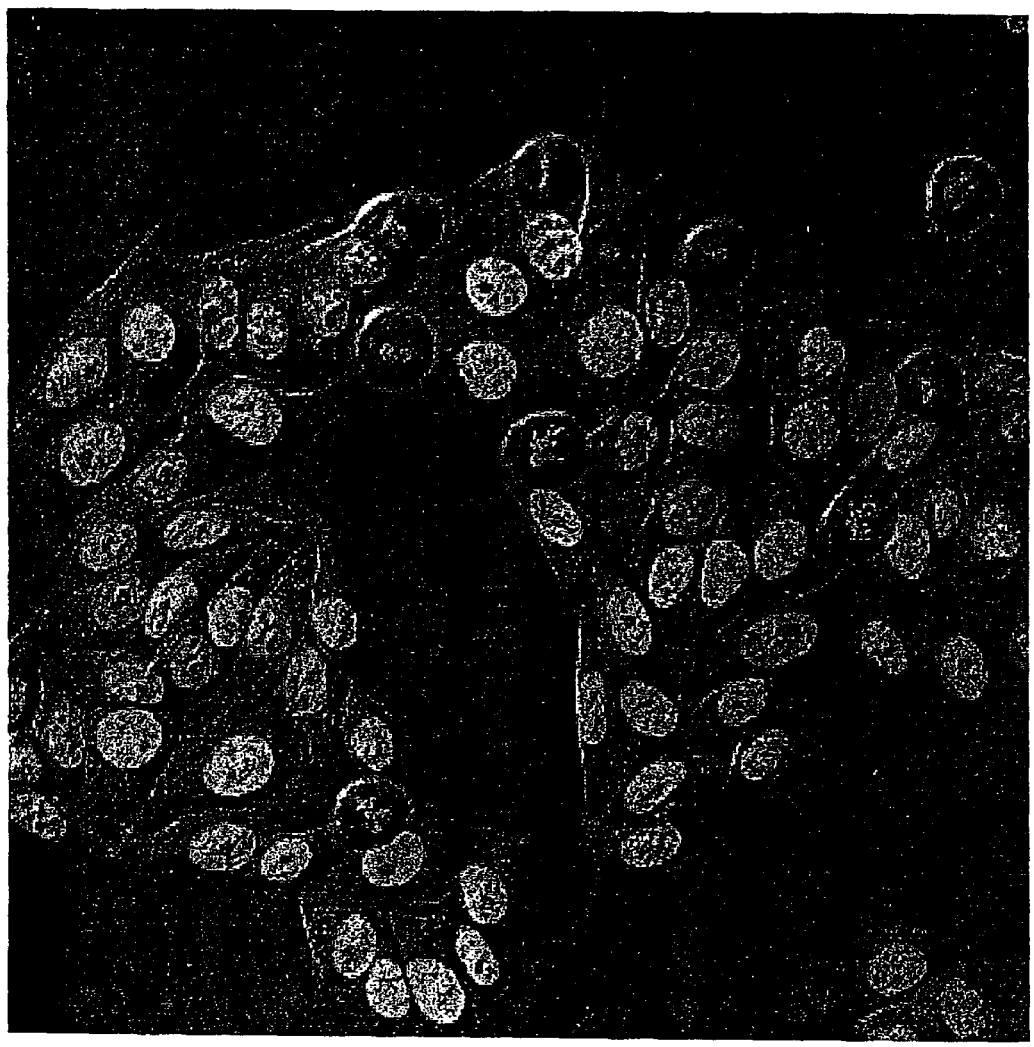
FIG. 9 shows H2B-GFP expressing cells. Confocal microscopic images of live HeLa cells with constitutive H2B-GFP expression. H2B-GFP fluorescence is shown with a reflectance mode image.

The human H2B gene was obtained by PCR amplification of human placental genomic DNA. Since histone H2B is a multicopy gene (Baxevanis, et al. (1997)), several clones were obtained by this PCR cloning. The amplified sequence with the highest homology to one of the reported H2B sequences (GenBank Accession Number X00088) (Zhong, et al. (1983)) was used to construct the H2B-GFP vector. The H2B gene was tagged either at its C-terminus (H2B-G) or N-terminus (G-H2B) with codon-optimized enhanced GFP (EGFP) (Yang, et al. (1996)) (FIG. 8), and these chimeric genes were cloned into mammalian expression vectors. Constructs were introduced into HeLa cells by transfection, and fluorescence microscopic observation indicates that both H2B-G and G-H2B proteins localized to interphase nuclei and mitotic chromosomes.

To further characterize the H2B-GFP protein, stable cell lines were made with H2B-GFP expression. Transfected cells were cultured with blasticidin for 2 weeks, and drug resistant colonies were analyzed by fluorescence microscopy to identify GFP positive colonies. GFP positive clones arose with equal frequencies using either H2B-G or G-H2B (~10%) of blasticidin-resistant colonies. Although it had been reported that stable GFP expressing cell lines were difficult to isolate (Shima, et al. (1997)), several stable cell lines with either H2B-G or G-H2B expression were observed.

I. H2B-GFP is Incorporated into Nucleosomes

Figure 10A:
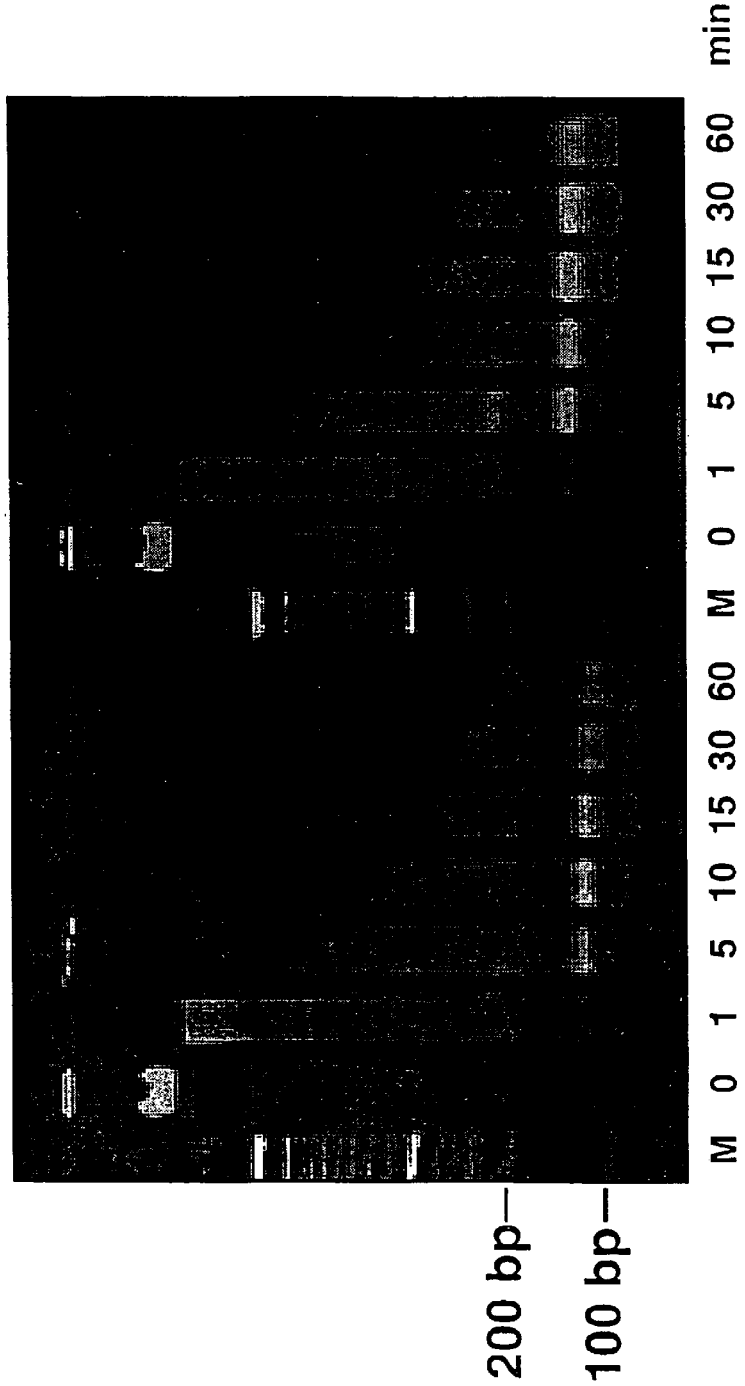

To determine if H2B-GFP is a component of nucleosome core particles, nucleosomal core particles were biochemically fractionated and analyzed for the presence of H2B-GFP. Mononucleosomes were generated by extensive micrococcal nuclease digestion of the isolated nuclei expressing H2B-GFP (FIG. 10A), and fractionated by sucrose gradient centrifugation in the presence of 0.5 M NaCl to dissociate histone H1 (Dubochet and Noll (1978) and Laybourn and Kadonaga (1991)). Electrophoretic analysis of the DNA showed that fractions 2 through 4 (predominantly fraction 3) contained DNA of the size expected for nucleosome core particle (146 bp) (FIG. 10D). The protein contents of the samples were analyzed by 15% SDS-PAGE. FIG. 10B shows the distribution of proteins across the gradient. H2B and H2B-GFP were specifically detected by Western analysis using anti human H2B antibody, demonstrating that H2B-GFP fusion protein is in mononuclesome fractions and its distribution parallels that of histones in the gradient (FIG. 10C).

J. H2B-GFP Incorporation does not Inhibit Cell Cycle Progression

Figures 11A, 11B:
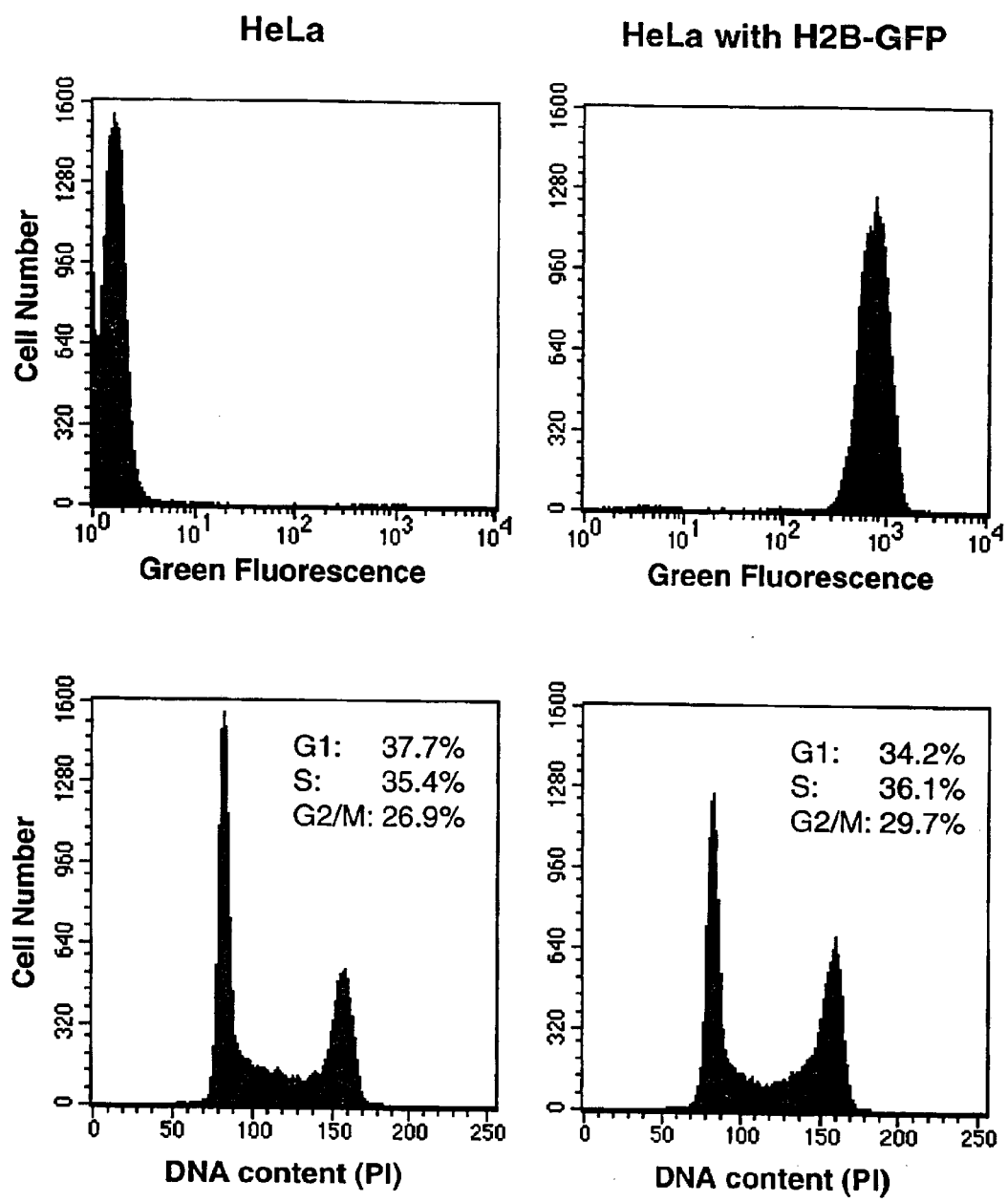
FIGS. 11A and 11B show H2B-GFP expression does not affect cell cycle progression.

Asynchronous HeLa cells and the transformant expressing H2B-GFP were fixed, stained with propidium iodide (PI), and analyzed by FACS. The green emission of GFP labeled cells produces an approximately three-log shift from parental HeLa cells (FIG. 11A). DNA content was determined by measuring red emission of PI (FIG. 11B). The results indicate that the cell cycle distribution of asynchronous HeLa cells expressing H2B-GFP is indistinguishable from that of the parental HeLa cells. The results clearly demonstrate that the H2B-GFP protein has little, if any, effect on cell cycle progression. Furthermore, like the parental cells, the H2B-GFP expressing cells were successfully synchronized using a double thymidine block strategy.

K. Discussion

These data demonstrate that H2B-GFP provides a novel strategy to fluorescently label chromosomes in living cells. Despite the large size of the GFP tag (239 amino acids), it has been shown in numerous cases that tagged proteins are functional and are targeted properly (Cubitt, et al. (1995) and Gerdes and Kaether (1996)). Apparently, both C-terminally (H2B-G) and N-terminally (G-H2B) tagged histones labeled chromosomes in transiently transfected cells, while establishing stable cell lines was accomplished using a C-terminally tagged histone. According to the X-ray crystal structure of the histone octamer (Arents, et al. (1991)), histones H3/H4 tetramer organize the path of the central turns of DNA in the nucleosomes, and H2A/H2B dimer bind at the both sides of H3/H4 tetramer. The primary interactions responsible for the stability of nucleosomes are electrostatic, because it has been long known that nucleosomes can be dissociated into their DNA and histone components by elevating ionic strength (Wolffe (1995)). Histone H1 as well as nonhistone proteins dissociates from the nucleosomes at 0.5M NaCl, but histones H2A/H2B and H3/H4 only dissociates at salt concentrations above 0.8M NaCl and 1.2M NaCl, respectively (Ohlenbusch, et al. (1967)). The experimental data demonstrated the co-fractionation of H2B-GFP with mononucleosomes under high ionic strength (0.5M NaCl). Therefore, it is likely that H2B-GFP protein is rather incorporated into nucleosome core particles than just attaching outside of nuclesome core particles.

The H2B-GFP strategy for analyzing chromosomes in living cells offers significant advantage to other methods. While vital fluorescent labeling of mammalian chromosomes has been demonstrated using Hoechst 33342 (Belmont, et al. (1989) and Hiraoka and Haraguchi (1996)), each cell line must be analyzed individually to optimize the time of drug exposure and concentration of the drug (Arndt-Jovin, et al. (1989)). Furthermore, since Hoechst 33342 is excited maximally near 350 mm and high intensities of UV irradiation can damage cells and produce cell cycle delay or arrest, the level of UV excitation must be carefully controlled. Intercalating DNA drugs, like dihydroethidium, may cause mutations in the DNA by interfering with DNA replication (Arndt-Jovin, et al. (1989)). Microinjection of rhodamine-labeled histones, successfully used for vital chromosome staining in *Drosophila* (Hiraoka, et al. (1989) and Minden (1989)), is not suitable for analyzing a large number of mammalian cells. In contrast to these methods, the enhanced GFP (Yang, et al. (1996)) employed herein is excited with blue light (490 nm), which is less damaging than UV light excitation required for Hoechst excitation. Photochemical damage by the formation of singlet oxygen through intersystem crossing is reduced by the cylindrical barrel structure of GFP, which protects the chromophore inside (Yang, et al. (1996) and Orrno (1996)). Since DNA is extremely susceptible to photodamage, GFP is an ideal protein tag for labeling DNA. Furthermore, a long duration time-lapse imaging was performed in which one image was collected per minute over a period of 17 hrs without photobleaching. Since H2B-GFP protein in the stable cell line is constitutively expressed by the integrated transgene, the cell line is particularly suitable for long-term analyses. As shown here, cell cycle distribution of the stable cell line with H2B-GFP expression is indistinguishable from that of the parental HeLa cells. Since the primary structure of histone proteins are well conserved among different species (Wells (1986)), the H2B-GFP described here is useful for cells of different species.

Analyses of the dynamics of chromosome behavior in vivo will benefit from the availability of GFP-tagged proteins that bind to specific chromosomal regions in combination with the global decoration provided by H2B-GFP. For example, centromeres in HeLa cells can be fluorescently labeled by the expression of centromere binding protein (CENP-B) fused to GFP. This enabled the motion of centromeres to be analyzed in mitotic and interphase cells (Shelby, et al. (1996)). Recently, a specific chromosome region has been fluorescently labeled using chromosomally integrated lac operator and in vivo expression of lac repressor-GFP fusion protein in CHO cells (Robinett, et al. (1996)) and in budding yeast (Straight, et al. (1996)). Implementation of different spectral variants of GFP for labeling a specific chromosome region together with H2B-GFP would enable one to monitor the behavior of specific sites in companion to global chromosomes simultaneously. For example, the spatial colocalization of centromeres with heterochromatin observed in fixed cells can be directly confirmed in living nuclei by tagging CENP-B with a different spectral variant of GFP.

There are numerous applications of the H2B-GFP vector and the methods of use thereof. As H2B-GFP intensities represent the chromosome condensation states, one can study chromosome condensation and decondensation (Hiraoka, et al. (1989)), nucleolar formation, and heterochromatin movement in interphase nuclei. Fragmented chromosomes can be visualized directly in apoptotic cells. Besides, in vivo visualization of chromosome segregation enables detailed analyses of dynamic movement of abnormal chromosomes. For example, chromosome bridge formation and micronucleation, which usually represent dicentric and acentric chromosomes (Shimizu, et al. (1996)), respectively, were visualized in living cells. Double minute chromosomes, harboring amplified genes, were also identified in living cells in spite of their smaller size compared to normal chromosomes. The H2B-GFP system is useful to analyze genomic instability, including formation of aneuploidy, gene amplification, and chromosome loss, which have been difficult to analyze using fixed chromosome spreads.

These results demonstrate that H2B-GFP fusion protein is incorporated into nucleosome core particles and allows high resolution imaging of chromosomes with preservation of nuclear and chromosomal structure. This enables the analysis various aspects of chromosome dynamics, including chromosome condensation, intranuclear chromatin structure, and segregation during mitosis.

It is to be understood that while the invention has been described in conjunction with the above embodiments, that the foregoing description and the following examples are intended to illustrate and not limit the scope of the invention. Other aspects, advantages and modifications within the scope of the invention will be apparent to those skilled in the art to which the invention pertains.

References

Arents, G., R. W. Burlingame, B. C. Wang, W. E. Love, E. N. Moudrianakis. 1991. "The nucleosomal core histone octamer at 3.1 A resolution: a tripartite protein assembly and a left-handed superhelix" *PNAS USA* 88:10148–52.

Arndt-Jovin, D. J., T. M. Jovin Eds. 1989. *Fluorescent Labeling and Microscopy of DNA*, pp 417–448.

Barker, P. E. 1982. "Double minutes in human tumor cells" *Cancer Genet Cytogenet.* 5:81–94.

Baxevanis, A. D., D. Jandsman. 1997. "Histone and histone fold sequences and structures: a database" *Nucleic Acids Res.* 25:272–3.

Belmont, A. S., M. B. Braunfeld, J. W. Sedat, D. A. Agard. 1989. "Large-scale chromatin structural domains within mitotic and interphase chromosomes in vivo and in vitro" *Chromosoma* 98:129–43.

Belmont, A. S. and K. Bruce. 1994. "Visualization of G1 chromosomes: a folded, twisted, supercoiled chromonema model of interphase chromatid structure" *J Cell Biol* 127:287–302.

Benner, S. E., G. M. Wahl and D. D. Von Hoff. 1991. "Double minute chromosomes and homogeneously staining regions in tumors taken directly from patients versus in human tumor cell lines" *Anti-Cancer Drugs.* 2:11–25.

Bondy, M. L., M. R. Spitz, S. Halabi, J. J. Fueger, S. P. Schantz, D. Sample and T. C. Hsu. 1993. "Association between family history of cancer and mutagen sensitivity in upper aerodigestive tract cancer patients" *Cancer Epidermal Biomarkers Prev.* 2:103–6.

Brison, O. 1993. "Gene amplification and tumor progression" *Biochem Biophys Acta* 1155:2541.

Canute, G. W., S. L. Longo, J. A. Longo, J. A. Winfield, B. H. Nevaldine and P. J. Hahn. 1996. "Hydroxyurea accelerates the loss of epidermal growth factor receptor genes amplified as double-minute chromosomes in human glioblastoma multiforme" *Neurosurgery* 39:976–83.

Carroll, S. M., M. L. DeRose, J. L. Kohnan, G. H. Nonet, R. E. Kelly and G. M. Wahl. 1993. "Localization of a bidirectional DNA replication origin in the native locus and in episomary amplified murine adenosine deaminase loci" *Mol Cell Biol* 13:2971–81.

Chen, C. and H. Okayama. 1987. "High-efficiency transformation of mammalian cells by plasmid DNA" *Mol Cell Biol* 7:2745–52.

Cohen. 1993. "Apoptosis" *Immunology Today* 14:126–130.

Cowell, J. K. 1982. "Double minutes and homogenously staining regions: gene amplification in mammalian cells" *Ann. Rev. Gen.* 16:21–59.

Cremer, T., A. Kurz, R. Zirbel, S. Dietzel, B. Rinke, E. Schrock, M. R. Speicher, U. Mathieu, A. Jauch and P. Emmerich. 1993. "Role of chromosome territories in the functional compartmentalization of the cell nucleus" *Cold Spring Harbor Symp. Quant. Biol.* 8:777–92.

Crook, T., J. A. Tidy and K. H. Vousden. 1991. "Degradation of p53 can be targeted by HPV E6 sequences distinct from those required for p53 binding and trans-activation" *Cell* 67:547–56.

Cubitt, A. B., R. Heim, S. R. Adams, A. E. Boyd, L. A. Gross, R. Y. Tsien. 1995. "Understanding, improving and using green fluorescent proteins" *Trends Biochem Sci* 20:448–55.

De, B. U. and A. H. Mintz. 1986. "Curvilinear, three-dimensional motion of chromatin domains and nucleoli in neuronal interphase nuclei" *Science.* 234:863–6.

Denko, N. C., J. Giaccia, J. R. Stringer and P. J. Stambrook. 1994. "The human Ha-ras oncogene induces genomic instability in murine fibroblasts within one cell cycle" *PNAS (USA)* 91:5124–8.

Di Leonardo, A., S. P. Linke, K. Clarkin and G. M. Wahl. 1994. "DNA damage triggers a prolonged p53-dependent G1 arrest and long-term induction of Cipl in normal human fibroblasts" *Genes Dev.* 8:2540–51.

Dini, L., S. Coppola, M. T. Ruzittu and L. Ghibelli. 1996. "Multiple pathways for apoptotic nuclear fragmentation" *Exp Cell Res.* 223:340–7.

Dubochet, J. and M. Noll. 1978. "Nucleosome arcs and helices" *Science* 202:280–6.

Duncan, A. M. and J. A. Heddle. 1984. "The frequency and distribution of apoptosis induced by three non-carcinogenic agents in mouse colonic crypts" *Cancer Lett* 23:307–11.

Duncan, A. M., J. A. Heddle and D. H. Blakey. 1985. "Mechanism of induction of nuclear anomalies by gamma-radiation in the colonic epithelium of the mouse" *Cancer Res.* 45:250–2.

Eckhardt, S. G., A. Dai, K. K. Davidson, B. J. Forseth, G. M. Wahl and D. D. Von Hoff. 1994. "Induction of differentiation in HL60 cells by the reduction of extrachromosomally amplified c-myc" *PNAS (USA)* 91:6674–6678.

Eki, T., T. Enomoto, Y, Murakami, F. Hanaoka and M, Yamada. 1987. "Characterization of chromosome aberrations induced by incubation at a restrictive temperature in the mouse temperature-sensitive mutant tsFT20 strain containing heat-labile DNA polymerase a" *Cancer Res.* 47:5162–5170.

Ferguson, M. and D. C. Ward. 1992. "Cell cycle dependent chromosomal movement in pre-mitotic human T-lymphocyte nuclei" *Chromosoma* 101:557–65.

Gavrieli, Y., Y. Sherman and S. S. Ben. 1992. "Identification of programmed cell death in situ via specific labeling of nuclear DNA fragmentation" *J Cell. Biol.* 119:493–501.

Gerdes, H. H. and C. Kaether. 1996. "Green fluorescent protein: applications in cell biology" *Febs Lett* 389:44–7.

Hamkalo, B. A., P. J. Farnham, R. Johnston and R. T. Schimke. 1985. "Ultrastructural features of minute chromosomes in a methotrexate-resistant mouse 3T3 cell line" *PNAS (USA)* 82:1026–30.

Heddle, J. A. and A. V. Carrano. 1977. "The DNA content of micronuclei induced in mouse bone marrow by gamma-irradiation: evidence that micronuclei arise from acentric chromosomal fragments" *Mutat. Res.* 44:63–9.

Heddle, J. A., M. C. Cimino, M. Hayashi, P. Romagna, M. D. Shelby, J. D. Tucker, P. Vanparys and J. T. MacGregor. 1991. "Micronuclei as an index of cytogenetic damage: past, present and future" *Environ Mol Mutage* 18:277–91.

Heddle, J. A., M. Hite, B. Kirkhart, K. Mavournin, J. T. MacGregor, G. W. Newell arid M. F. Salamone. 1983. "The induction of micronuclei as measure of genotoxicity" A report of the U.S. Environmental Protection Agency Gene-Tox Program *Mutat Res,* 123:61–118.

Hiraoka, Y. and T. Haraguchi. 1996. "Fluorescence imaging of mammalian living cells" *Chromosome Res* 4:173–6.

Hiraoka, Y., J. S. Minden, J. R. Swedlow, J. W. Sedat, D. A. Agard. 1989. "Focal points for chromosome condensation and decondensation revealed by three-dimensional in vivo time-lapse microscopy" *Nature* 342:293–6.

Huang, L.-C., K. C. Clarkin and G. M. Wahl. 1996. "p53 dependent cell cycle arrests are preserved in DNA-activated protein kinase deficient mouse fibroblasts" *Cancer Res.* 56:2940–2944.

Izumi, M., H. Miyazawa, T. Kamakura, I. Yamaguchi, T. Endo, F. Hanaoka. 1991. "Blasticidin S-resistance gene (bsr): a novel selectable for mammalian cells" [published erratum appears in Exp Cell Res 1993 February; 204(2) :388] *Exp Cell Res* 197:229–33.

Jackson, J. F, and E. G. Clement. 1974. "Letter Nuclear projections and chromosome abnormalities" *Lancet* 2:1270–1.

Kastan, M. B., Q. Zhan, W. S. El-Deiry, F. Carrier, T. Jacks, W. V. Walsh, B, S. Plunkett, B. Vogelstein and A. J. Fonace. 1992. "A mammalian cell cycle checkpoint pathway utilizing p53 and GADD45 is defective in ataxia-telangiectasia" *Cell.* 7:587–97.

Kuerbitz, S. J., B. S. Plunkett, W. V. Walsh and M. B. Kastan. 1992. "Wild-type p53 is a cell cycle checkpoint determinant following irradiation" *PNAS (USA)* 89:7491–5.

Lawce, H. J. and G. Brown. 1991. *Harvesting Slide Making and Chromosome Elongation Techniques* Raven Press, Ltd. New York.

Laybourn, P. J. and J. T. Kadonaga. 1991. "Role of nucleosomal cores and histone H1 in regulation of transcription by RNA polymerase II" *Science* 254:238–45.

Levan, A. and G. Levan. 1978. "Have double minutes functioning centromeres?" *Hereditas.* 88:81–92.

Levan, G., N. Mandahl, U. Bregula, G. Klein and A. Levan. 1976. "Double minutes chromosomes are not centromeric regions of the host chromosomes" *Hereditas.* 83:83–90.

Linke, S., P., K. C. Clarkin, A. DiLeonardo, A. Tsou and G. M. Wahl. 1996. "A reversible p53-dependent G0/G1 cell cycle arrest induced by ribonucleotide depletion in the absence of detectable DNA damage" *Genes and Dev.* 10:934–947.

Linke, S. P., K. C. Clarkin and G. M. Wahl. 1997. "p53 mediates permanent arrest over multiple cell cycles in response to gamma radiation" *Cancer Res.* 7:1171–1179.

Livingstone, L. R., A. White, J. Sprouse, E. Livanos, T. Jacks and T. D. Tlsty. 1992. "Altered cell cycle arrest and gene amplification potential accompany loss of wild-type p53" *Cell* 70: 923–35.

Lo, C. F. and M. Fraccaro. 1974. "Letter: Nuclear projections in tumour cells" *Lancet.* 2:847.

Manuelidis, L. and J. Borden. 1988. "Reproducible compartmentalization of individual chromosome domains in human CNS cells revealed by in situ hybridization and three-dimensional reconstruction" *Chromosoma.* 96:397–410.

Miele, M., S. Bonatti, P. Menichini, L. Ottaggio and A. Abbondandolo. 1989. "The presence of amplified regions affects the stability of chromosomes in drug-resistant Chinese hamster cells" *Mutat Res.* 219:171–8.

Mizushima, S. and S. Nagata. 1990. "pEF-BOS, a powerful mammalian expression vector" *Nucleic Acids Res* 18:5322.

Moroi, Y., A. L. Hartman, P. K. Nakane, E. M. Tan. 1981. "Distribution of kinetochore (centromere) antigen in mammalian cell nuclei" *J Cell Biol* 90:254–9.

Ohlenbusch, H. H., B. M. Olivera, D. Tuan, N. Davidson. 1967. "Selective dissociation of histones from calf thymus nucleoprotein" *J Mol Biol* 25:299–315.

Ormo, M., A. B. Cubitt, K. Kallio, L. A. Gross, R. Y. Tsien, S. J. Remington. 1996. "Crystal structure of the *Aequorea victoria* green fluorescent protein" [see comments] *Science* 273:1392–5.

Pedeutour, F., R. F. Suijkerbuijk, A. Forus, G. J. Van, Van, de, Klundert, W. J. M. Coindre, G. Nicolo, F. Collin, H. U. Van, K. Huffermann. 1994. "Complex composition and coamplification of SAS and MDM2 in ring and giant rod marker chromosomes in well-differentiated liposarcoma" *Genes Chromosom Cancer* 10:85–94.

Robinett, C. C., A. Straight, G. Li, C. Willhelm, G. Sudlow, A. Murray, A. S. Belmont. 1996. "In vivo localization of DNA sequences and visualization of large-scale chromatin organization using lac operator/repressor recognition" *J Cell Biol* 135:1685–700.

Roser, M., A. Bohm, M. Oldigs, K Weichenthal., U. Reimers, P. U. Schmidt, E. W. Breitbart and H. W. Rudiger. 1989. "Ultraviolet-induced formation of micronuclei and sister chromatid exchange in cultured fibroblasts of patients with cutaneous malignant melanoma" *Cancer Gene Cytogenet.* 41:129–37.

Ruddle, F. H. 1962. "Nuclear Bleb: A stable interphase marker in established line of cells in vitro" *J. Nat'l Cancer Inst.* 28:1247–1251.

Satoh, M. S, and T. Lindahl. 1992. "Role of poly (ADP-ribose) formation in DNA repair" *Nature* 356:356–8.

Scheffner, M., B. A. Werness, J. M. Huibregtse, A, J. Levine and P. M. Howley. 1990. "The E6 oncoprotein encoded by human papillomavirus types 16 and 18 promotes the degradation of p53" *Cell* 63:1129–36.

Schubert, I. and J. L. Oud. 1997. "There is an upper limit of chromosome size for normal development of an organism" *Cell* 88:515–520.

Shelby, R. D., K. M. Hahn, K. F. Sullivan. 1996. "Dynamic elastic behavior of alpha-satellite DNA domains visualized in situ in living human cells" *J Cell Biol* 135:545–57.

Shima, D. T., K. Haldar, R. Pepperkok, R. Watson, G. Warren. 1997. "Partioning of the golgi apparatus during mitosis in living HeLa cells" *J Cell Biol* 137:1211–28.

Shima, H., M. Nakayasu, S. Aonuma, T. Sugimura and M. Nagao. 1989. "Loss of the MYC gene amplified in human HL-60 cells after treatment with inhibitors of poly(ADP-ribose) polymerase or with dimethyl sulfoxide" *PNAS (USA)* 86:7442–7445.

Shimizu, N., T. Kanda and G. M. Wahl. 1996. "Selective capture of acentric fragments by micronuclei provides a rapid method for purifying extrachromosomally amplified DNA" *Nature Genetics* 12: 65–71.

Shimizu, N., H. Nakamura, T. Kadota, K. Kitajima, T. Oda, T. Hirano and H. Utiyama. 1994. "Loss of amplified c-myc genes in the spontaneously differentiated HL-60 cells" *Cancer Res.* 54:3561–3567.

Shimizu, N., T. Kanda, G. M. Wahl. 1996. "Selective capture of acentric fragments by micronuclei provides a rapid method for purifying extrachromosomally amplified DNA" *Nat Genet* 12:65–71.

Snapka, R. M. 1992. "Gene amplification as a target for cancer chemotherapy" *Oncol. Res.* 4:145–50.

Snapka, R. M, and A. Varshavsky. 1983. "Loss of unstably amplified dihydrofolate reductase genes from mouse cells is greatly accelerated by hydroxyurea" *PNAS (USA)* 80:7533–7.

Stein, S. J., S. L. Stein, J. B. Lian, T. J. Last, T. Owen and L. McCabe. 1994. *Synchronization of normal diploid and transformed mammalian cells* Academic Press, San Diego.

Straight, A. F., A. S. Belmont, C. C. Robinett, A. W. Murray. 1996. "GFP tagging of budding yeast chromosomes reveals that protein-protein interactions can mediate sister chromatid cohesion" *Curr Biol* 6:1599–608.

Sullivan, et al. 1994. "Human CENP-A contains a histone H3 related histone fold domain that is required for targeting to the centromere" *J. Cell Biol.* 127:581–92.

Takebe, Y, M. Seiki, J. Fujisawa, P. Hoy, K. Yokota, K. Arai, M. Yoshida, N. Arai. 1988. "SR alpha promoter: an efficient and versatile mammalian CDNA expression system composed of the simian virus 40 early promoter and the R-U5 segment of human T-cell leukemia virus type 1 long terminal repeat" *Mol Cell Biol* 8:466–72.

Toledo, F., R. D. Le, G. Buttin and M. Debatisse. 1992. "Co-amplified markers alternate in megabase long chromosomal inverted repeats and cluster independently in interphase nuclei at early steps of mammalian gene amplification" *Embo J.* 11:2665–73.

Von Hoff, D., D. Needham-VanDevanter, J. Yucel, B. Windle and G. Wahl. 1988. "Amplified human MYC oncogenes localized to replicating subnucroscopic circular DNA molecules" *PNAS (USA)* 85:4804–4808.

Von Hoff, D. D., J. R. McGill, B. J. Forseth, K. K. Davidson, T. P. Bradley, D. R. Van Devanter and G. M. Wahl. 1992. "Elimination of extrachromosomally amplified MYC genes from human tumor cells reduces their tumorigenicity" *PNAS (U.S.A)* 89:8165–8169.

Von Hoff, D. D., T. Waddelow, B. Forseth, K. Davidson, J. Scott and G. M. Wahl. 1991. "Hydroxyurea accelerates the loss of extrachromosomally amplified genes form tumor cells" *Cancer Research.* 51:6273–6279.

Vourc'h, C., D. Tarusico, A. L. Boyle and D. C. Ward. 1993. "Cell cycle-dependent distribution of telomeres, centromeres, and chromosome-specific subsatellite domains in the interphase nucleus of mouse lymphocytes" *Exp Cell Res.* 205:142–51.

Wahl, G. M. 1989. "The importance of circular DNA in mammalian gene amplification" *Cancer Res.* 49:1333–1340.

Wells, D. E. 1986. "Compilation analysis of histones and histone genes" *Nucleic Acids Res* 14:119–49.

White, A. E., E. M. Livanos and T. D. Tlsty. 1994. "Differential disruption of genomic integrity and cell cycle regulation in normal human fibroblasts by the HPV oncoproteins" *Genes and Development* 8:666–77.

White, E. 1994. "Tumor biology. p53, guardian of Rb" *Nature* 371:21–2.

Wolffe, A. 1995. *Chromatin. Structure and Function*, Second Edition; Academic Press Yang, F., L. G. Moss, J. G. N. Phillips. 1996. "The molecular structure of green fluorescent protein" *Nat Biotechnol* 14:1246–1251.

Yang, T. T., L. Cheng, S. R. Kain. 1996. "Optimized codon usage and chromophore mutations provide enhanced sensitivity with the green fluorescent protein" *Nucleic Acids Res* 24:4592–3.

Yin, Y., M. A. Tainsky, F. Z. Bischoff, L. C. Strong and G. M. Wahl. 1992. "Wild-type p53 restores cell cycle control and inhibits gene amplification in cells with mutant p53 alleles" *Cell.* 70:93748.

Zhong, R., R. G. Roeder, N. Heintz. 1983. "The primary structure and expression of four cloned human histone genes" *Nucleic Acids Res* 11:7409–25.

What is claimed is:

1. A method to identify an agent that increases or decreases the amount of double minute chromosomes or extrachromosomal DNA in a cell, comprising contacting the cell with the agent, wherein the cell expresses a labeled histone that associates with double minute chromosomes or extrachromosomal DNA to form a labeled complex; and comparing the amount of the labeled complex contained in the cell contacted with the agent with the amount of labeled complex contained in a cell that was not contacted with the agent.

2. The method of claim 1, wherein the cell is alive when the amount of labeled complex is compared.

3. The method of claim 1, wherein the cell is dead when the amount of labeled complex is compared.

4. The method of claim 1, wherein the labeled histone comprises a fluorescently labeled protein.

5. The method of claim 1, wherein the labeled histone is fused to a fluorescent protein.

6. The method of claim 5, wherein the fluorescent protein is *Aequorea victoria* green fluorescent protein, *Aequorea victoria* cayenne fluorescent protein or *Aequorea victoria* yellow fluorescent protein.

7. The method of claim 1, wherein the histone is H3, H4, H2A or H2B.

8. The method of claim 1, wherein the histone is H2B.

9. The method of claim 1, wherein the cell contains an oncogene.

10. The method of claim 1, wherein the cell lacks at least one functional tumor suppressor gene.

11. The method of claim 1, wherein the cell expresses a non-functional p53 protein.

12. The method of claim 1, wherein the cell is a cancer cell.

13. The method of claim 1, wherein the cell is a human cell.

14. The method of claim 1, wherein the cell is a neoplastic cell.

15. The method of claim 1, wherein the labeled complex is compared with fluorescence microscopy or flow cytometry.

16. The method of claim 1, further comprising determining if the cell has undergone reversion of a neoplastic phenotype, differentiation or apoptosis.

17. The method of claim 1, wherein the comparing is done in vitro, in vivo or ex vivo.

* * * * *